United States Patent [19]
Cimochowski et al.

[11] Patent Number: 5,967,986
[45] Date of Patent: *Oct. 19, 1999

[54] ENDOLUMINAL IMPLANT WITH FLUID FLOW SENSING CAPABILITY

[75] Inventors: George E. Cimochowski, Dallas, Pa.; George W. Keilman, Woodinville, Wash.

[73] Assignee: VascuSense, Inc., Woodinville, Wash.

[*] Notice: This patent is subject to a terminal disclaimer.

[21] Appl. No.: 08/978,038

[22] Filed: Nov. 25, 1997

[51] Int. Cl.⁶ .................................. A61B 5/02; A61B 8/04
[52] U.S. Cl. ........................... 600/454; 600/504; 600/505
[58] Field of Search .................................. 600/437, 438, 600/454, 455, 459, 462, 467, 381, 504, 505; 334/24 R

[56] References Cited

U.S. PATENT DOCUMENTS

| | | | |
|---|---|---|---|
| 3,731,184 | 5/1973 | Goldberg et al. | 324/34 R |
| 4,733,665 | 3/1988 | Palmaz | 128/343 |
| 5,063,081 | 11/1991 | Cozzette et al. | 427/2 |
| 5,195,984 | 3/1993 | Schatz | 606/195 |
| 5,200,051 | 4/1993 | Cozzette et al. | 204/403 |
| 5,466,575 | 11/1995 | Cozzette et al. | 435/6 |
| 5,807,258 | 9/1998 | Cimochowski et al. | 600/454 |

FOREIGN PATENT DOCUMENTS

| | | | |
|---|---|---|---|
| WO97/33513 | 9/1997 | WIPO | A61B 5/00 |
| WO98/08466 | 3/1998 | WIPO | A61F 2/06 |

OTHER PUBLICATIONS

Andle, J.C., et al., Acoustic Wave Biosensors, 1995 IEEE Ultrasonics Symposium, pp. 451–460.

Beusekom, H.M.M., et al., Biocompatibility of phosphorylcholine coated stents in a porcine coronary model, Abstracts from the 70$^{TH}$ Scientific Sessions, p. I–289, 1609.

Biode Home Page, http://www.biode.com, Nov. 15, 1997, 7pp.

(List continued on next page.)

*Primary Examiner*—Francis J. Jaworski
*Assistant Examiner*—Ali M. Imam
*Attorney, Agent, or Firm*—Ronald M. Anderson

[57] ABSTRACT

A stent or graft stent energized from an external power source is provided with one or more sensors to sense a parameter, producing a signal that is transmitted outside a vessel in which the stent is implanted. At least a portion of a body of the stent or an insulated electrical conductor comprises a plurality of turns that serve as an RF antenna. An expandable mesh or helical coils that form the stent body may serve as the antenna or it may comprise a separate insulated conductor. The RF antenna receives energy electromagnetically coupled to the antenna from an external (or implanted) coil and conveys a data signal corresponding to the parameter sensed by the sensor(s) on the stent or stent graft to a monitor disposed outside the patient's body. In one form of the invention, a plurality of conformal array transducers are used to produce and sense ultrasonic waves that are affected by a fluid flowing through a lumen of the stent. This transducer determines fluid flow or fluid velocity. In other embodiments, one or more integrated circuit (IC) sensors are used to sense other physical or biological parameters in the proximity of the stent, producing signals that are multiplexed by an electronics circuit and transmitted to the external monitor/power supply.

54 Claims, 11 Drawing Sheets

U.S. PATENT DOCUMENTS

Christensen, D. et al., Biosensor Development at the University of Utah, IEEE Engineering in Medicine and Biology, Jun./Jul. 1994, pp. 388–395.

Dillon, A.E., et al., Minimally Invasive Surgery with Coronary and Peripheral Stents, Published on the Internet, May 20, 1996, available Oct. 1997, at http://www.bae.ncsu.edu/bae/courses/bae465/1995_projects/dill, 25 pp.

Erickson, K.A. et al., Evaluation of a Novel Point–of–Care System, the i–STAT Portable Clinical Analyzer, Clinical Chemistry, vol. 39, No. 2, 1993, pp. 283–287.

Henry, M., et al., Initial Experience with Corvita Endoluminal Graft in Peripheral Arteries, Abstracts from the 70$^{TH}$ Scientific Sessions, I–441, 2463.

Herrmann, R.A., et al., Comparisons of the Thrombogenicity of Steel and Gold–Surface Coronary Stents with a Biodegradable, Drug Releasing Coating in a Human Stasis Model, Abstracts from the 70$^{TH}$ Scientific Sessions, I–722, Supplement I, 4048.

Hetke, J.F. et al., Silicon Ribbon Cables for Chronically Implantable Microelectrode Arrays, IEEE Transactions on Biomedical Engineering, vol. 41, No. 4, Apr. 1994, pp. 314–321.

Knutti, J.W., et al., Integrated Circuit Implantable Telemetry Systems, Engineering in Medicine and Biology Magazine, Mar. 1983, IEEE, pp. 47–50.

Mackay, R.S., Bio–Medical Telemetry, Sensing and Transmitting Biological Information from Animals and Man, IEEE Engineering in Medicine and Biology Society, Sponsor, William Perkins, Editor in Chief, ©1993, IEEE Press, New York, 4pp.

Pepine, C.J., et al., Coronary Artery Stents, ACC Expert Consensus Document, Internet Article, at http://www–east.elsevier.com, 1996, Elsevier, 23pp.

Shults, M.C., et al., A Telemetry–Instrumentation System for Monitoring Multiple Subcutaneously Implanted Glucose Sensors, IEEE Transactions on Biomedical Engineering, vol. 41, No. 10, Oct. 1994, pp. 937–942.

SRI Center for Medical Technology–Research, Advanced Technologies Division, Medical Technology, Internet document, at http://os.sri.com/medical/research.html, printed Nov. 15, 1997, 2pp.

Inway®–Plus Urological Program, Internet printout, at http://www.pfm–ag.de/urology.htm, printed Nov. 15, 1997, 2pp.

World Medical Mfg. Corp. Brochure, TALENT Endovascular Spring Graft Systems, Internet printout, at http://www-.medicom.com/world, printed Nov. 17, 1997; 10pp.

Zierhofer, C.M., et al., High–Efficiency Coupling–Insensitive Transcutaneous Power and Data Transmission Via an Inductive Link, IEEE Transactions on Biomedical Engineering, vol. 37, No. 7, Jul. 1990, pp. 716–722.

ENDOLUMINAL IMPLANT WITH FLUID FLOW SENSING CAPABILITY

FIELD OF THE INVENTION

The present invention generally relates to the use of sensors to monitor fluid flow through a body passage, and more specifically, to the use of sensors to monitor flow and velocity of a fluid, and/or other parameters, including biochemical levels, temperature, pressure, strain, and the degree and type of deposits within a lumen of an endoluminal implant such as a stent or other type of endovascular conduit.

BACKGROUND OF THE INVENTION

In the 1970s, the technique of percutaneous transluminal coronary angioplasty (PTCA) was developed for the treatment of atherosclerosis. Atherosclerosis is the build-up of fatty deposits or plaque on the inner walls of a patient's arteries; these lesions decrease the effective size of the artery lumen and limit blood flow through the artery, prospectively causing a myocardial infarction or heart attack if the lesions occur in coronary arteries that supply oxygenated blood to the heart muscles. In the angioplasty procedure, a guide wire is inserted into the femoral artery and is passed through the aorta into the diseased coronary artery. A catheter having a balloon attached to its distal end is advanced along the guided wire to a point where the sclerotic lesions limit blood flow through the coronary artery. The balloon is then inflated, compressing the lesions radially outward against the wall of the artery and substantially increasing the size of its internal lumen, to improve blood circulation through the artery.

Increasingly, stents are being used in place of or in addition to PTCA for treatment of atherosclerosis, with the intent of minimizing the need to repeatedly open an atherosclerotic artery. Although a number of different designs for stents exist in the prior art, all are generally configured as elongate cylindrical structures that can assume two different states, one having a substantially greater diameter than the other. A stent is implanted in a patient using an appropriate delivery system for the type of stent being implaced within the patient's arterial system. There are two basic types of stents—those that are expanded radially outward due to the force from an inflated angioplasty type balloon, such as the Palmaz-Schatz stent, the Gianturco-Roubin stent, and the Strecker stent, and those that are self expanding, such as the Maass double helix spiral stent, the Nitinol stent (made of nickel titanium memory alloy), the Gianturco stent, and the Wallstent. Problems with the Maass double helix spiral stent and the Nitinol stent have limited their use.

Stents are sometimes used following a PTCA procedure if the artery is totally occluded or if the lesions have occluded a previously placed surgical graft. Typically, a stent constrained within an introducer sheath is advanced to a site within the patient's artery through a guide catheter. For the balloon expanded type, after the introducer sheath is retracted, a balloon disposed inside the stent is inflated to a pressure ranging from about six to ten atmospheres. The force produced by the inflated balloon expands the stent radially outward beyond its elastic limit, stretching the vessel and compressing the lesion to the inner wall of the vessel. A self expanding stent expands due to spring force following its implacement in the artery, after a restraining sheath is retracted from the compressed stent, or in the case of the Nitinol version, the stent assumes its expanded memory state after being warmed above the transition temperature of the Nitinol alloy (e.g., above 30° C.). Following the expansion process, if the balloon type is used, the balloon is removed from inside the stent and the catheter and other delivery apparatus is withdrawn. The lumen through the vessel should be substantially increased, improving blood flow.

After a stent or other endoluminal device is implanted, a clinical examination and either an angiography or ultrasonography morphological procedure is performed to evaluate the success of the procedure in opening the diseased artery or vessel. These tests are typically repeated periodically, e.g., at six-month intervals, since restenosis of the artery may become necessary. Due to the nature of the tests, the results of the procedure can only be determined qualitatively, but not quantitatively with any degree of accuracy or precision. It would clearly be preferable to monitor the flow of blood through the stent after its implacement in a vessel, both immediately following the stenosis and thereafter, either periodically or on a continuous basis. Measurements of volumetric rate and/or flow velocity of the blood through the stent would enable a medical practitioner to much more accurately assess the condition of the stent and of the artery in which the stent is implanted. Currently, no prior art mechanism is available that is implantable inside a blood vessel for monitoring the flow conditions through a stent.

Other parameters measurable within a stent or other type of endoluminal implant are also of interest and could be monitored using one or more appropriate sensors or transducers. For example, monitoring pressure at the distal and proximal end of the lumen in the implant and determining the differential pressure can provide an indication of fluid velocity through the lumen. Temperature can also be used to monitor fluid flow based by applying heat to the fluid within the lumen and monitor the rate at which the temperature of the fluid decreases as the fluid flows from the lumen of the implant. Integrated circuit (IC) transducers are currently known and available for sensing the levels of many different types of biochemical substances, such as glucose, potassium, sodium, chloride ions, and insulin. Any of these IC sensors could be provided in an endoluminal implant to monitors these parameters.

Since it is impractical to pass a conductor through the wall of an artery or vessel for long periods of time, use of a conventional sensor that produces signals indicative of flow through a stent, which must be conveyed through a conductor that extends through the wall of the vessel and outside the patient's body is not a practical solution to this problem. Also, any active flow indicative sensor must be energized with electrical power. Again, it is not practical to supply power to such a sensor through any conductor that perforates the vessel wall or that passes outside the patient's body. Battery power for such a sensor would quickly be exhausted and a battery would likely be too bulky to include inside an artery.

In addition to stents, the generic term endoluminal implant encompasses stent grafts, which are also sometime referred to as "spring grafts." A stent graft is a combination of a stent and a synthetic graft that is typically endoscopically implanted at a desired point in a vessel. Helically coiled wired comprising the stent are attached to the ends of the synthetic graft and are used to hold the graft in position. Sometimes, hooks are provided on the stent to ensure that the graft remains in the desired position within the vessel. Clearly, it would also be desirable to monitor the status of flow and other parameters through a stent graft, just as noted above in regard to a stent.

Endoluminal implants are used in other body passages in addition to blood vessels. For example, they are sometimes used to maintain an open lumen through the urethra, or through the cervix. A stent placed adjacent to an enlarged prostate gland can prevent the prostate from blocking the flow of urine through the urinary tract. Tracheal and esophageal implants are further examples of endoluminal implants. In these and other uses of an endoluminal implant, provision for monitoring parameters related to the status of flow and other conditions in the patient's body would be desirable. Information provided by monitoring such parameters can enable more effective medical treatment of a patient.

SUMMARY OF THE INVENTION

In accord with the present invention, an endoluminal implant is defined that is adapted to be inserted into a body passage and to determine a condition of fluid flow through the endoluminal implant within the body passage. The endoluminal implant includes a generally tubular shaped member having two states, including a compact state in which the member has a first cross-sectional size and an expanded state in which the member has a second cross-sectional size that is substantially greater than the first cross-sectional size. The member includes an electrical conductor. A sensor on the implant is adapted to monitor a parameter related to fluid flow through the member, producing a signal indicative of the parameter. A data transmitter is coupled to the sensor and to the member, so as to receive the signal from the sensor and then to transmit electromagnetic data corresponding to the signal. The data transmitter is adapted to transmit the electromagnetic data outside the body passage in which the endoluminal implant is installed, using the electrical conductor of the member as an antenna.

The endoluminal implant further includes an external coil adapted to be disposed proximate to the member, but outside the body passage. The external coil receives the electromagnetic data transmitted from the member. A monitor that includes a power source is coupled to the external coil for displaying an indication of the parameter, as a function of the electromagnetic data. The external coil electromagnetically transfers electrical power to the member from the power source.

In one preferred embodiment, the member comprises a spiral winding. In another preferred embodiment, the member comprises a helical braid.

In one form of the invention, the sensor comprises an ultrasonic transmitter that produces an ultrasonic waveform directed through an interior portion of the member. The ultrasonic waveform is affected by a fluid flowing through the interior portion of the member to provide an indication of the condition of the fluid flow through the member. In one embodiment of this configuration, the ultrasonic transmitter also operates as an ultrasonic receiver, to receive an echo of the ultrasonic waveform that is reflected from the fluid flow through the member. Alternatively, the sensor further comprises an ultrasonic receiver that receives the ultrasonic waveform produced by the transmitter after the ultrasonic waveform is affected by the fluid flow through the member. The ultrasonic receiver then produces the signal indicative of the parameter. Preferably, the ultrasonic transmitter and ultrasonic receiver each comprise a conformal array of a plurality of spaced-apart, flexible transducer elements that have a curved configuration generally conforming to a curvature of the member. The conformal arrays are disposed either inside or outside of the member, and the conformal array for the ultrasonic transmitter is configured so that it produces ultrasonic waveforms, which propagate through the interior portion of the member in a predefined direction relative to a longitudinal axis of the member. For this form of the invention, the parameter is preferably either a fluid velocity or a fluid volumetric flow rate. The ultrasonic receiver is preferably disposed on an opposite side of the member from where the ultrasonic transmitter is located.

In another form of the invention, the sensor comprises a distal and a proximal pressure transducer. The distal pressure transducer is exposed to a fluid pressure of the fluid flow through an interior portion of the member adjacent to where the fluid exits the member, and the proximal pressure transducer is exposed to a fluid pressure of the fluid flow through the interior portion of the member adjacent to where the fluid enters the member. The signal produced by the sensor is thus indicative of a differential pressure corresponding to a difference between the proximal and distal pressures respectively sensed by the proximal and distal pressure transducers.

Preferably, the endoluminal implant comprises either a stent or a stent graft. If the member is not itself used for the antenna, the electrical conductor is coiled about the member in a plurality of turns, to form the antenna. In this case, the member includes a break point at a joint fastened with a nonconductive material. The break point prevents the member from acting as a shorted turn that would reduce the efficacy of the antenna.

A further aspect of the present invention is directed to a method for conveying a parameter sensed in the vicinity of an endoluminal implant adapted to be moved to a treatment site inside a body passage, to an external location disposed outside the body passage. The steps of the method are generally consistent with the functions of the components of the endoluminal implant discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

The present invention is employed for monitoring parameters proximate to an endoluminal implant. As used herein and in the claims that follow, the term endoluminal implant broadly encompasses stents, graft stents (sometime referred to as "spring grafts"), and other types of devices that are inserted into a lumen or body passage and moved to a desired site to provide a structural benefit to the lumen. To simplify the disclosure of the present invention, most of the following discussion is directed to embodiments comprising a stent.

The parameters that are monitored are preferably directed to determining the status of the fluid flow through the endoluminal implant. For example, the rate or velocity of fluid flow through a body passage in which the stent has been positioned can be monitored to determine the extent of fatty growth or tissue deposits in a blood vessel in which the stent has been implanted to treat atherosclerosis. By monitoring these parameters which are indicative of blood flow through the lumen of the stent and the blood vessel in which it is implanted, a medical practitioner can evaluate the need for further treatment or determine whether restenosis has occurred. Moreover, other physical and biological parameters can be monitored using one or more appropriate sensors attached to a stent.

If the status of fluid flow through a stent that has been implanted in a patient's vascular system (or some other parameter that is sensed proximate the stent) is to be monitored for an extended period of time, the stent will likely need to receive electrical power from an external source to energize the circuitry used to monitor the parameter and must convey data indicating the status of fluid flow (or other parameter) from the implanted stent to an external monitoring device that is disposed outside the patient's body. In many cases, it may be desirable to monitor one or more parameters at multiple stents or at multiple locations on a single stent. Thus, the specific transducer or sensor employed to monitor a desired parameter must be selectable so that the data signal indicating the parameter can be transmitted outside the patient's body. However, in some cases, only a single transducer may be required to monitor a parameter such as fluid volumetric flow or velocity, which is indicative of the internal condition of the stent and of the blood vessel in which it is implanted.

Figure 1:
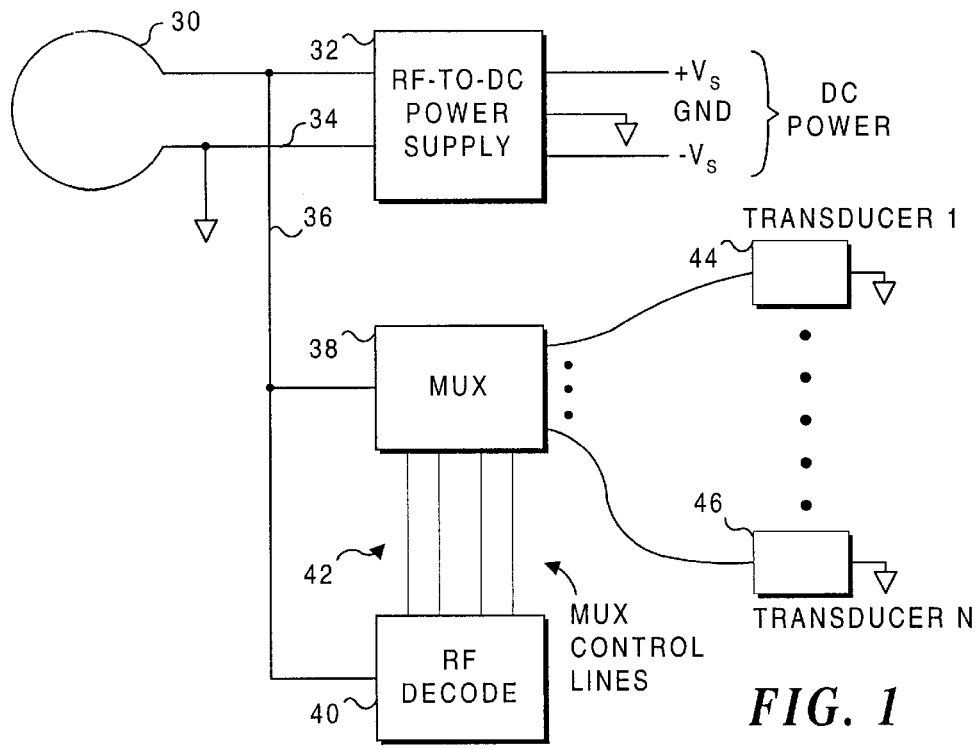
FIG. 1 is a block diagram showing a first embodiment of an electronic circuit for monitoring a parameter proximate to a stent with a selected transducer from a plurality of transducers.

FIG. 1 illustrates a first embodiment of an implanted electronics system for monitoring one or more parameters, applicable to the situation in which n transducers are included on one or more stents implanted in the patient's body. Variations of the electronic circuit shown in FIG. 1 are discussed below to accommodate specific conditions. In addition, other embodiments of electronic circuits are illustrated in FIGS. 2–6. These embodiments, like that of FIG. 1, are useful for providing power to transducers that monitor fluid flow or velocity through a stent, and for transmitting data signals from the transducers outside a patient's body to an external remote monitoring console. Some of these circuits are better suited for certain types of measurements than others, and again, variations in the implanted electronic circuits are discussed below, where appropriate to explain these distinctions.

Each of the circuits shown in FIGS. 1–6 are intended to be implanted within the patient's body and left in place at least during the period in which the flow conditions through one or more stents or other parameters are monitored. Although separate functional blocks are illustrated for different components of the implanted electronic circuits in these Figures, any of the implanted electronic circuits can be implemented in one or more application specific integrated circuits (ASICs) to minimize size and cost, which is particularly important when the electronic circuits are integral with a stent. The electronic circuits can be either included within the wall of a stent, or may be simply implanted adjacent to blood vessel(s) in which the stent(s) is/are disposed. However, if not integral with the stent, the circuits must be electromagnetically coupled to the transducers, since it is impractical to extend any conductor through a wall of the blood vessel in which a stent is implanted, to couple to circuitry disposed outside the blood vessel. Therefore, the circuits are preferably integral with the stent so that they are implanted with the stent inside the blood vessel.

Each of the circuits shown in FIGS. 1–6 includes an RF antenna 30, which is connected through lines 34 and 36 to an RF-to-DC power supply 32. The RF antenna is preferably part of the expandable structure of the stent body or may instead be added to a stent, for example, by threading an insulated wire through the expandable wall of a stent. The RF antenna preferably comprises a helical coil or saddle-shaped coil, as explained in greater detail below. The power supply rectifies and filters an RF excitation signal supplied from an external source to RF antenna 30, providing an appropriate voltage DC power signal for the other components of the circuits illustrated in these Figures. In the simplest case, the RF-to-DC power supply would only require rectifiers and filters as appropriate to provide any needed positive and negative supply voltages, $+V_S$ and $-V_S$. However, it is also contemplated that the power supply may provide for a DC-to-DC conversion capability in the event that the electromagnetic signal coupled into RF antenna 30 is too weak to provide the required level of DC voltage for any component. This conversion capability would increase the lower voltage produced by the direct coupling of the external RF excitation signal received by the RF antenna, to a higher DC voltage. Details of the RF-to-DC power supply are not shown, since such devices are well known to those of ordinary skill in constructing power supplies. It is also contemplated that it may be necessary to limit the maximum amplitude of the RF input signal to the RF-to-DC power supply to protect it or so that excessive DC supply voltages are not provided to the other components. Alternatively, each component that must be provided with a limited DC voltage supply may include a voltage limiting component, such as a zener diode or voltage regulator (neither shown).

The RF-to-DC power supply may include a battery or a capacitor for storing energy so that it need not be energized when monitoring the flow status, or at least, should include sufficient storage capability for at least one cycle of receiving energy and transmitting data relating to the parameter being monitored. Although a storage battery can be included, size limitations may prohibit any significant storage capacity. Instead, a relatively small capacitor could provide the required storage capability. Neither a battery or power storage capacitor are illustrated in the Figures, since they are well known to those of ordinary skill.

An additional element that is common to each of the circuits shown in FIGS. 1–6 is an RF decode section 40, which is used for generating control signals that are responsive to information encoded in the external RF excitation signal received by RF antenna 30. This information can be superimposed on the RF excitation signal, e.g., by amplitude or frequency modulating the signal received.

Figure 2:
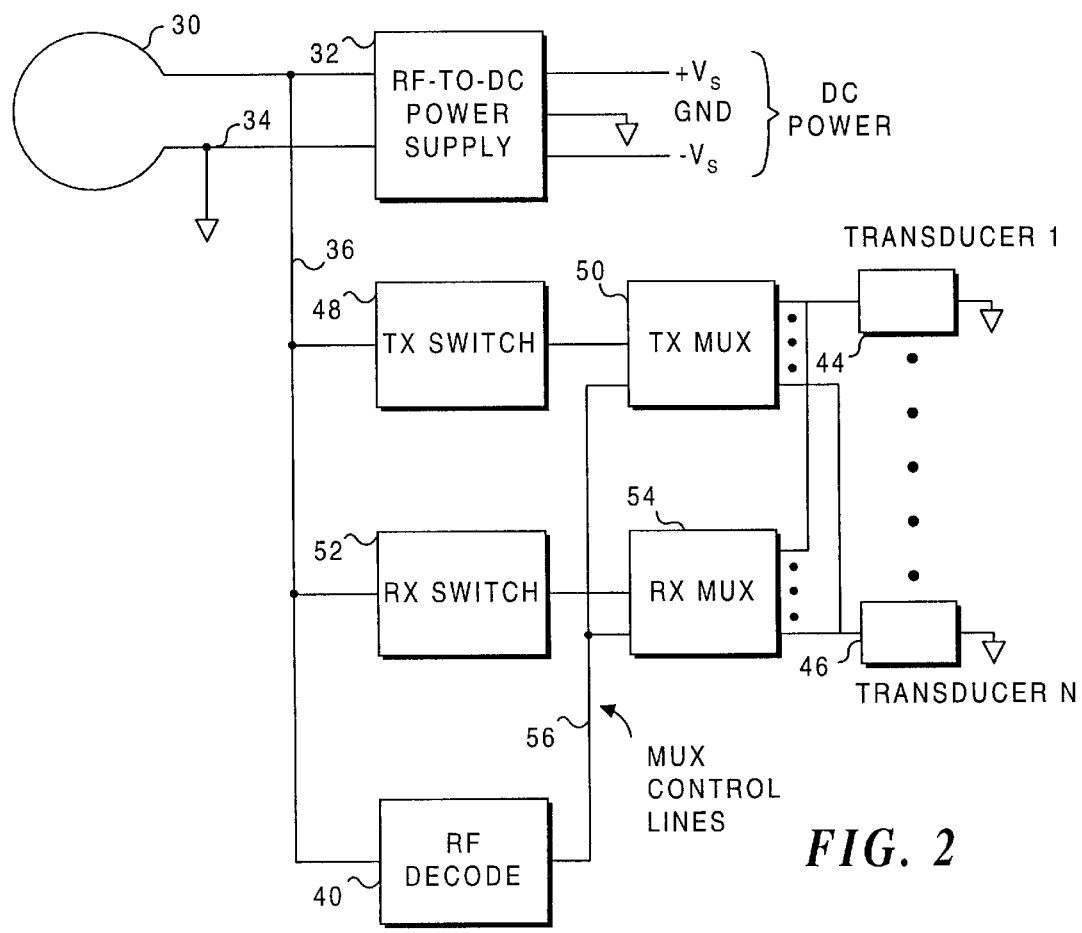
FIG. 2 is a block diagram of a second embodiment of an electronic circuit for monitoring one or more parameters using separate multiplexors for transmit and receive functions.
Figure 3:
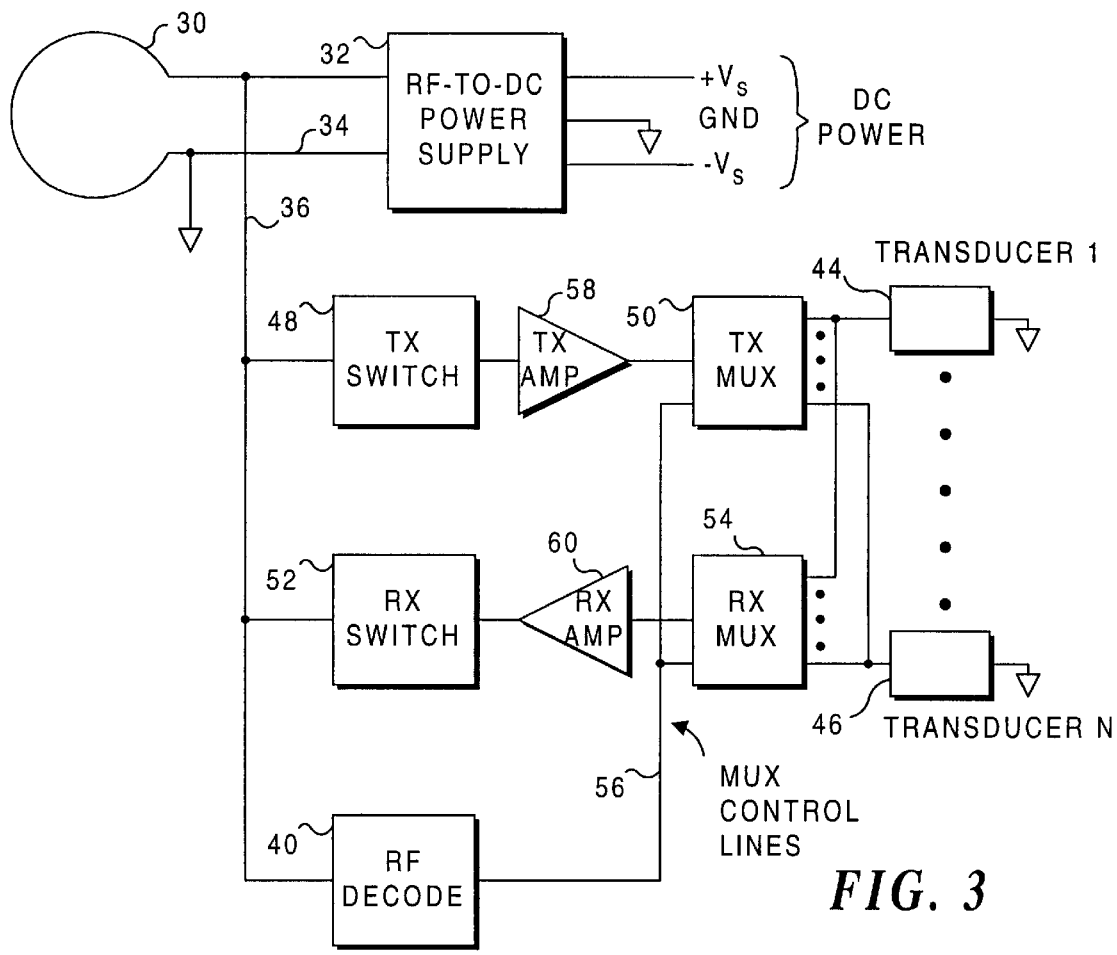
FIG. 3 is a block diagram of a third embodiment of an electronic circuit for monitoring one or more parameters using separate multiplexors and amplifiers for transmit and receive functions.

In regard to the circuits shown in FIGS. 1–3, when used for monitoring fluid velocity or flow, the RF excitation frequency is the same as the frequency used to excite a selected ultrasonic transducer to produce an ultrasonic wave that propagates through a lumen of the stent being monitored, and for conveying data from a transducer that receives the ultrasonic waves. This approach generally simplifies the electronic circuitry but may not provide optimal performance. Therefore, FIGS. 4 and 5 disclose electronic circuitry in which the RF excitation frequency used to provide power to the RF-to-DC power supply and to provide control signals to RF decode section 40 is decoupled from the frequency that is used for exciting the ultrasonic transducers and modulating the data that they provide for transmission to a point outside the patient's body. Although other types of transducers may be employed that are energized with an RF excitation frequency, such as surface acoustic wave transducers that are used for sensing chemical substances, many transducers many only require a DC voltage to sense a desired parameter such as pressure or temperature.

Details of the Electronic Circuits

Referring now to FIG. 1, line 36 from RF antenna 30 is connected to a multiplexor (MUX) 38 to convey signals from a selected one of a plurality of n transducers 44–46 (which are disposed at different points on a stent) that are coupled to the MUX. To select the transducer that will provide the data signal related to a parameter at a specific location on a stent, RF decode section 40 provides a control signal to MUX 38 through MUX control lines 42. The control signal causes the MUX to select a specific transducer that is to be excited by the RF signal received by RF antenna 30 and further, causes the MUX to select the transducer that will provide the data signal for transmission outside the patient's body (or at least outside the blood vessel in which the stent is disposed) via RF antenna 30.

In addition to ultrasonic transducers, the electronic circuit shown in FIG. 1 can also be used in connection with pressure transducers. For ultrasonic transducers, the circuit is perhaps more applicable to the Doppler type for use in monitoring fluid velocity through a stent. If a single-vessel pulse Doppler transducer is used, the same transducer can be used for both transmission and reception of the ultrasonic wave, thereby eliminating the need for MUX 38. In the event that the transducers shown in FIG. 1 are used for transit time flow measurements, it will normally be necessary to use MUX 38 to switch between the transducer used for transmitting the ultrasonic wave and that used to receive the ultrasonic wave, which may present some problems in connection with switching speed, power consumption, and switching transient recovery.

For a single-vessel transit time measurement, a pair of opposed transducers that are disposed on opposite sides of the stent are typically used. In order to acquire bi-directional fluid flow data, the direction of the ultrasound wave propagation must be known, i.e., the direction in which the ultrasound wave propagates relative to the direction of fluid flow through the vessel. In this case, MUX 38 is required. However, for single-vessel applications in which the fluid flow is in a single known direction, the transducers that are disposed on opposite sides of the stent can be electrically connected in parallel or in series, eliminating any requirement for MUX 38. The RF-to-DC power supply and RF decode sections could also then be eliminated, since the retarded and advanced transit time signals would be superimposed on the same RF waveform transmitted by RF antenna 30 outside the patient's body (or outside the blood vessel in which the stent is disposed, if an internal coil is implanted adjacent the blood vessel near where the stent is implanted). Although this modification to the electronic circuit shown in FIG. 1 would not permit the direction of fluid flow through a stent to be determined, the retarded and advanced transit time signals would interfere as they propagate in time, and their interference can be used to estimate the magnitude of fluid flow through the stent.

In FIG. 2, an electronic circuit is shown that uses a transmit multiplexor (TX MUX) 50 and a receive multiplexor (RX MUX) 54. In addition, a transmit (TX) switch 48 and a receive (RX) switch 52 couple line 36 to the TX MUX 50 and RX MUX 54, respectively. RF decode section 40 responds to instructions on the signal received from outside the patient's body by producing a corresponding MUX control signal that is conveyed to TX MUX 50 and RX MUX 54 over MUX control lines 56 to select the desired transducers.

When ultrasonic signals are being transmitted by one of the selected transducers 1 through n, TX switch 48 couples the RF excitation signal received by RF antenna 30 to the transducer that is transmitting the ultrasonic signal, which is selected by TX MUX 50. The TX switch is set up to pass excitation signals to the selected transducer only if the signals are above a predetermined voltage level, for example, 0.7 volts. Signals below that predetermined voltage level are blocked by the TX switch. Similarly, RX switch 52 connects the transducer selected by RX MUX 54 to RF coil 30 and passes only signals that are below the predetermined voltage level, blocking signals above that level. Accordingly, the RF signal used to excite a first transducer selected by TX MUX 50 passes through TX switch 48 and the lower amplitude signal produced by a second transducer selected by RX MUX 54 in response to the ultrasonic signal transmitted through the stent is conveyed through RX MUX 54 and RX switch 52 and transmitted outside the patient's body through RF coil 30.

The electronic circuit shown in FIG. 3 is similar to that of FIG. 2, but it includes a transmit amplifier (TX AMP) 58 interposed between TX switch 48 and TX MUX 50, and a receive amplifier (RX AMP) 60 interposed between RX MUX 54 and RX switch 52. TX AMP 58 amplifies the excitation signal applied to the transducer selected by TX MUX 50 for producing the ultrasonic wave that is propagated through the interior lumen of a stent. Similarly, RX AMP 60 amplifies the signal produced by the transducer selected by RX MUX 54 before providing the signal to the RX switch for transmission outside the patient's body (or at least, outside the blood vessel in which the stent is implanted). Again, the circuit shown in FIG. 3 is most applicable to transit time flow measurements and employs the same frequency for both the RF excitation signal that supplies power to RF-to-DC power supply 32 and the signal applied to a selected one of transducers 44–46 to generate the ultrasonic wave propagating through the stent.

Figure 4:
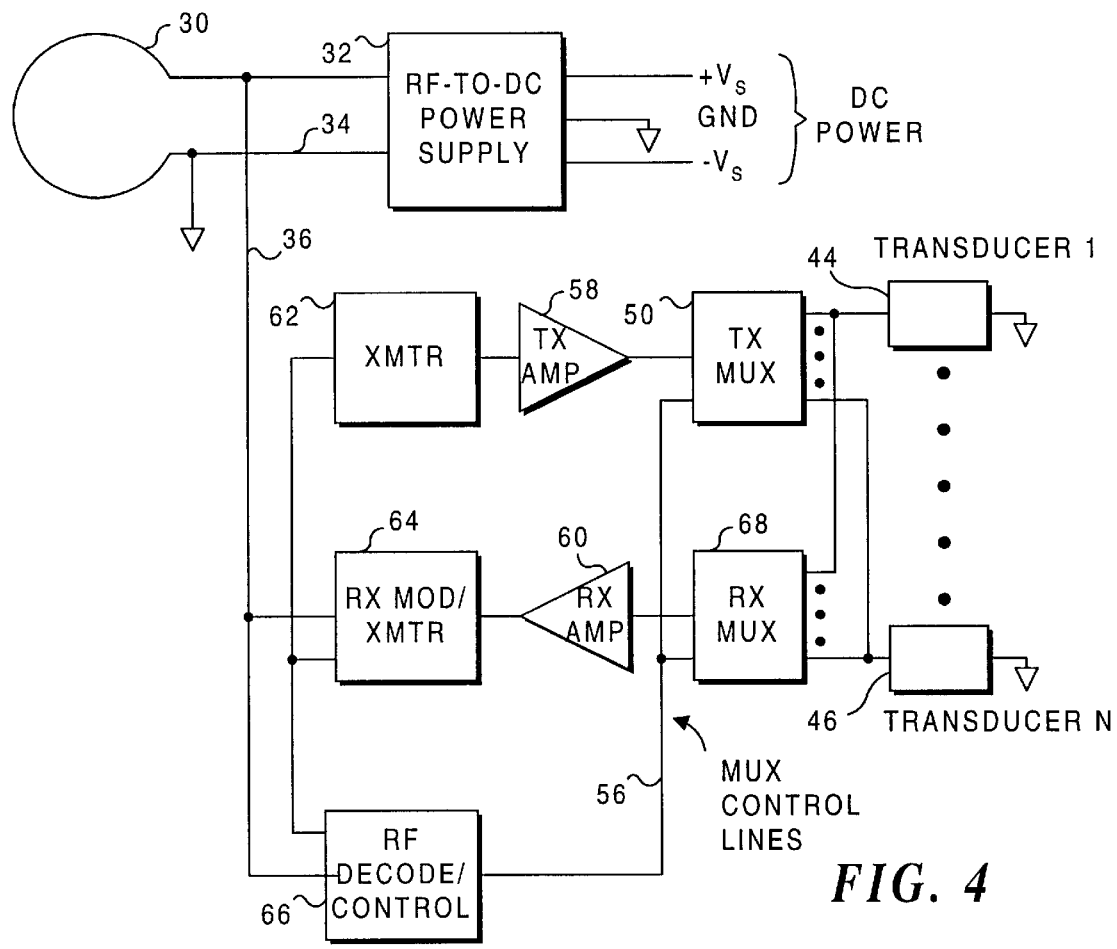
FIG. 4 is a block diagram of a fourth embodiment of an electronic circuit for monitoring one or more parameters, employing a local transmitter to excite a selected transducer, and a modulator/transmitter for transmitting signals from the transducers.

In contrast to the electronic circuits shown in FIGS. 1–3, the circuit shown in FIG. 4 enables the RF excitation frequency applied to RF-to-DC power supply 32 to be decoupled from the signal applied to excite any selected one of transducers 44–46. Similarly, the signal produced by the transducer receiving the ultrasonic waves propagating through the stent is at a different frequency than the RF excitation frequency. In FIG. 4, a transmitter (XMTR) 62 and a receive modulator/transmitter (RX MOD/XMTR) 64 are coupled to and controlled by an RF decode/control section 66. The RF decode/control section determines when the excitation frequency is generated for application to a selected transmit transducer and when the signal produced by the transducer selected to receive the ultrasonic wave is used for modulating the RF signal applied to RF antenna 30. An advantage of this approach is that the RF power delivered to RF antenna 30 is at an optimal frequency for penetration through the patient's body, thereby improving the efficacy with which the RF energy couples to a specific depth and location within the body. Another reason for using this approach is to enable selection of a particular frequency as necessary to comply with radio frequency allocation bands for medical equipment. Similarly, the frequency applied to any selected transducers 44 and 46 to stimulate their production of ultrasonic waves can be optimal for that purpose. Assuming that the two frequency bands, i.e., the RF excitation frequency band for the signal applied to the power supply and the frequency band applied to excite the transducers, are sufficiently separated, the RF power delivery can occur simultaneously with the excitation of a selected transducer and the reception of the ultrasonic waves by another selected transducer. Accordingly, more RF power can be coupled into the system from the external source than in the electronic circuits shown in FIGS. 1–3.

The control signals that are supplied to RF decode/control section 66 via RF antenna 30 can be conveyed using nearly any kind of modulation scheme, e.g., by modulating the RF excitation that powers the device, or by sending a control signal on a separate and distinct RF frequency. Also, the signals that are received from the transducer in response to the ultrasonic wave that is propagated through the stent can be transmitted through the RF antenna at a different frequency than the incoming excitation frequency, thereby eliminating interference between the power supply and data signal transmission functions.

The electronic circuit shown in FIG. 4 is most applicable to transit time flow measurements in which pairs of transducers are selected for transmitting and receiving the ultrasonic wave that propagates through the one or more stents on which the transducers are installed. RF decode/control section 66 can be employed to control TX MUX 50 and RX MUX 68 to interchange the transducers used for transmission and reception of the ultrasonic wave on successive pulses. Using this technique, the direction of the ultrasonic wave propagation through the stent is changed on alternating pulses of ultrasonic waves, enabling transit time difference information to be gathered without requiring further multiplexor programming information to be transmitted between successive ultrasonic wave pulses. This approach greatly improves the data gathering efficiency of the electronic circuit shown in FIG. 4 compared to the previously described electronic circuits of FIGS. 1–3.

Figure 5:
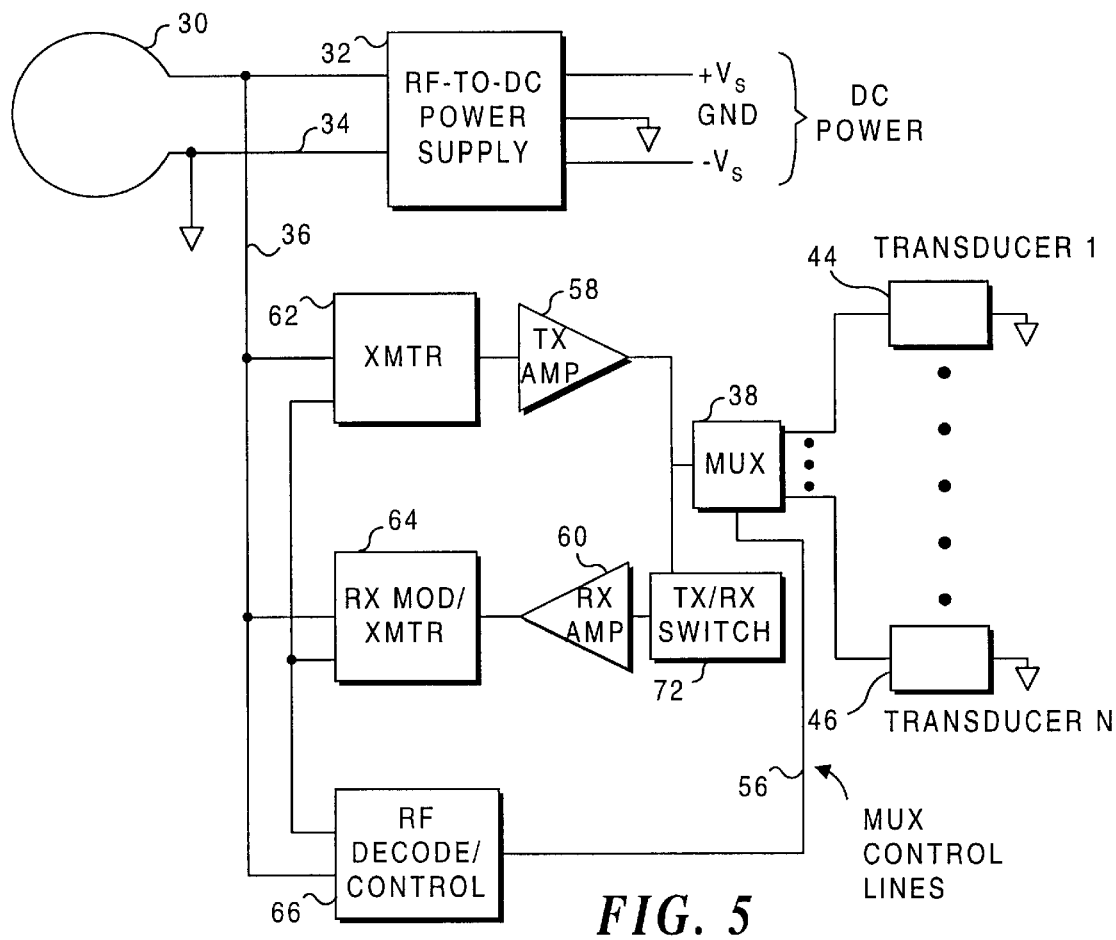
FIG. 5 is a block diagram of a fifth embodiment of an electronic circuit for monitoring one or more parameters in a stent, where one transducer is selected for transmitting and receiving, and a modulator/transmitter is used for transmitting the signal produced by the receiving transducer.

To further improve the electronic circuit shown in FIG. 4 for use in sensing fluid velocity through a stent using a Doppler technique, the modification shown in FIG. 5 is made. In FIG. 5, a TX/RX switch 72 is added so that the circuit transmits and receives through the same transducer. As a result, separate transmit and receive multiplexors are not required. Instead, MUX 38 is used to select the specific transducer for receiving the RF excitation signal produced by XMTR 62 so that the transducer produces an ultrasonic wave and then receives the echo from fluid flowing through the stent to produce a receive data signal that is output through RX MOD/XMTR 64. TX/RX switch 72 prevents the signal applied by TX AMP 58 from overdriving the input to RX AMP 60, effectively isolating the RX AMP during the time that the RF signal is applied to the transducer to excite it so that it produces the ultrasonic wave. However, the echo signal received by the transducer is allowed to reach RX AMP 60 when TX/RX switch 68 changes state (from transmit to receive). Generally, the electronic circuit shown in FIG. 5 has the same benefits as described above in connection with the circuit shown in FIG. 4. RF decode/control section 66 responds to the information received from outside the patient's body that determines which one of transducers 44-46 is selected at any given time by producing an appropriate MUX control signal that is supplied to MUX 38 over MUX control lines 56.

It is also contemplated that RF decode/control section 66 may cause MUX 38 to select a different transducer for producing/receiving the ultrasonic waves after a predefined number of transmit/receive cycles have elapsed. For example, a different transducer may be selected after eight cycles have been implemented to transmit an ultrasonic wave into the stent and to receive back the echoes from the fluid flowing through the stent. By collecting data related to the status of flow through a stent in this manner, it becomes unnecessary to send programming information to RF decode/control section 66 after each cycle of a transmission of the ultrasonic wave into the fluid in the stent and reception of the echo. Also, by carrying out a predefined number of transmit/receive cycles for a given transducer that has been selected by MUX 38 and averaging the results, a more accurate estimate of fluid velocity through the stent can be obtained than by using only a single transmission and reception of an ultrasonic wave. Since the signal required to instruct RF decode/control section 66 to change to the next transducer is only required after the predefined number of cycles has been completed, the data gathering efficiency of the implanted electronic circuit is improved.

Figure 6:
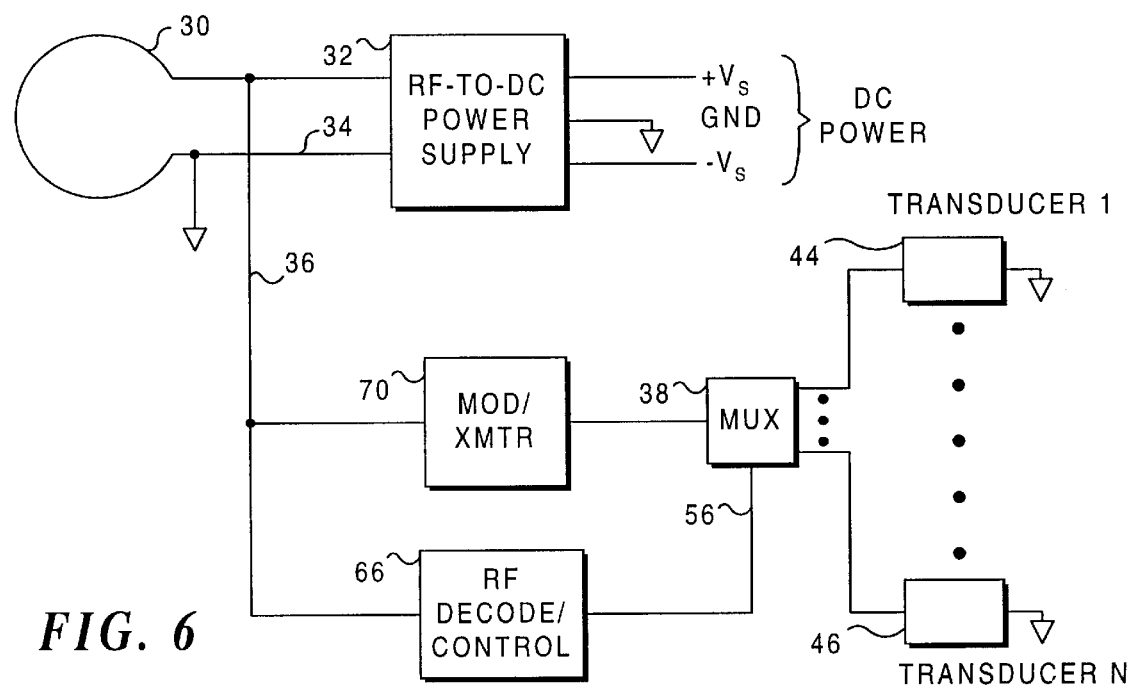
FIG. 6 is a block diagram of a sixth embodiment of an electronic circuit for monitoring one or more parameters in a stent, wherein one of a plurality of transducers is selectively coupled to a modulator/transmitter for transmitting a signal indicative of a parameter.

As noted above, transducers 44-46 shown in FIGS. 1–5 need not be ultrasonic transducers; FIG. 6 illustrates an electronic circuit that is particularly applicable for use with transducers 44-46 comprising pressure sensors. Such pressure sensors could be disposed within the wall of a stent to sense the pressure of fluid flowing through the stent at one or more points. MUX 38 is used for selecting a specific pressure transducer to provide a data signal that is transmitted to the outside environment via RF antenna 30. In this circuit shown in FIG. 6, a modulator/transmitter (MOD/XMTR) 70 receives the signal from the transducer selected by MUX 38 in response to the MUX selection signal provided over MUX control lines 56 from RF decode/control section 66 and using the signal, modulates an RF signal that is supplied to antenna 30. The RF signal transmitted by antenna 30 thus conveys the data signal indicating pressure sensed by the selected transducer. In many cases, it will be preferable to monitor the pressure at the distal and proximal ends of a stent in order to enable the differential pressure between these ends to be determined. This differential pressure is indicative of the extent to which any blockage in the interior lumen of the stent is impeding fluid flowing through the lumen. In most cases, parameters such as fluid flow or velocity are better indicators of the status of flow through the stent.

RF Antenna and External Coil Embodiments

FIGS. 7–12 illustrate details of several different embodiments for the RF antenna that is part of the stent implanted within a patient's body for receiving RF energy to provide power for the implanted electronic circuits discussed above and for transmitting data relating to the condition of flow and/or other parameter(s) sensed by one or more stents that have been installed within the patient's vascular system. Optimization of RF coupling between the RF antenna on the stent and the external coil is partially dependent upon the propagation characteristics of the human body. Since the body tissue is largely comprised of water, the relative dielectric constant of flesh is approximately equal to that of water, i.e., about 80. Also, the permeability of tissue comprising a body is approximately equal to one, i.e., about that of free space. The velocity of propagation of an RF signal through the body is proportional to the inverse square root of the dielectric constant and is therefore about 11% of the velocity of the signal in free space. This lower velocity reduces the wavelength of the RF signal by an equivalent factor. Accordingly, the wavelength of the RF signal transferred between the implanted RF antenna on a stent and the external coil would be a design consideration if the separation distance between the two is approximately equal to or greater than one-quarter wavelength. However, at the frequencies that are of greatest interest in the present invention, one-quarter wavelength of the RF coupling signal should be substantially greater than the separation distance between the RF antenna on the stent and the external coil.

The penetration of RF fields in the human body has been studied extensively in conjunction with magnetic resonance imaging (MRI) systems. RF attenuation increases with frequency, but frequencies as high as 63 MHz are routinely used for whole-body imaging, although some attenuation is observed at the center of the torso at this upper frequency limit. In addition, MRI safety studies have also provided a basis for determining safe operating limits for the RF excitation that define the amplitude of excitation safely applied without harm to the patient.

It is contemplated that for stent implants placed deep within the abdomen of a patient, RF excitation and frequencies used for communicating data related to the fluid flow through a stent and/or other parameters sensed proximate the stent can be up to about 40 MHz, although higher frequencies up to as much as 100 MHz may be feasible. At 40 MHz, the wavelength of the RF excitation signal in tissue is about 82 cm, which is just that point where wavelength considerations become an important consideration. For shallow implants, RF excitation at a much higher frequency may be feasible. For example, to provide energy to stents that are disposed within a blood vessel only a few millimeters below the epidermis and to receive data from transducers associated with such stents, excitation frequencies in the range of a few hundred MHz may be useful. The dielectric properties of tissue have been studied to at least 10 GHz by R. Pethig, *Dielectric and Electronic Properties of Biological Materials*, Wiley Press, Chichester, 1979 (Chapter 7). Based on this study, no penetration problems are anticipated in the frequency range of interest. The dielectric constant of tissue decreases to about 60 at a frequency of 100 MHz and is about 50 at 1 GHz, but this parameter has little effect on power/data signal coupling.

Figure 7:
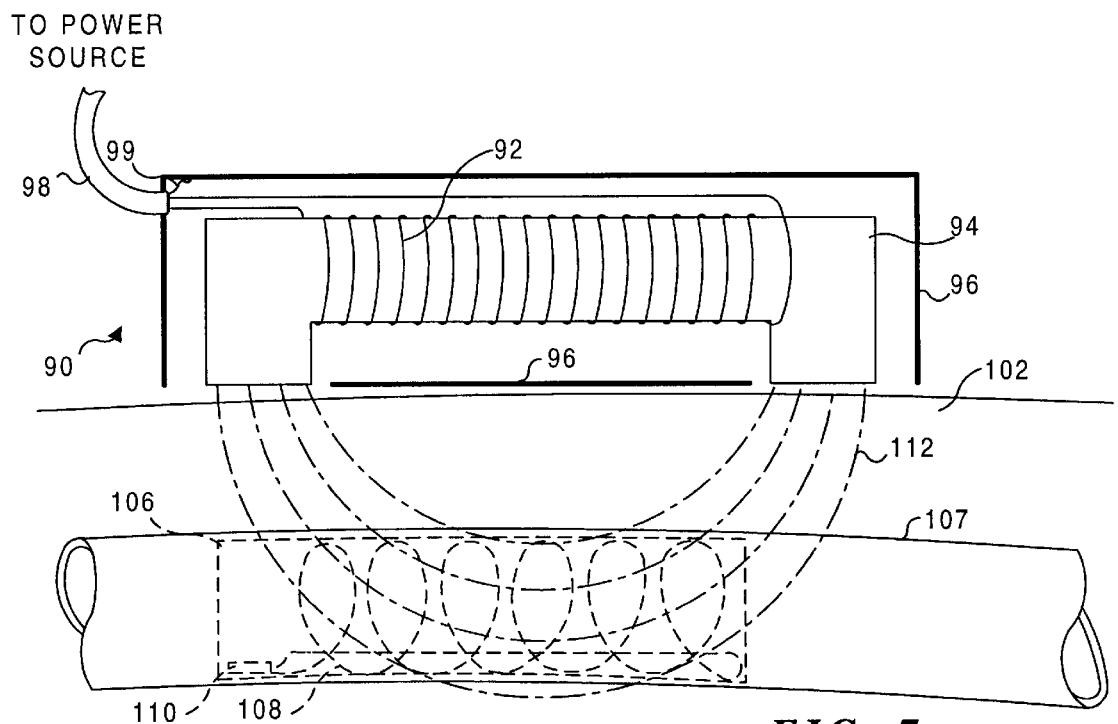
FIG. 7 is a cross-sectional view of a radio frequency (RF) antenna in a stent that is implanted in a blood vessel, and an external coil that is electromagnetically coupled to the RF antenna.

The external coil and RF antenna shown in FIG. 7 represent one embodiment of each of these components that can be used for coupling electrical energy and conveying data signals across a skin interface 102 for applications in which the RF antenna is implanted relatively close to the surface of the skin. For example, RF antenna 30 and external coil 90 would provide the coupling required for a system used to monitor a stent implanted in an artery near the skin surface. A winding 92 is wrapped around a core 94 forming an external coil 90 and each end of the winding is coupled to a power source through a cable 98.

Although the external coil and the RF antenna need not be identical in size, it is generally true that coupling will be optimal if the two devices are of approximately the same dimensions and if the longitudinal axis of the external coil is generally aligned with that of the RF antenna. By observing the strength of the signal transmitted from RF antenna 30, it should be possible to position external coil 90 in proper alignment with the RF antenna so that the efficiency of the electromagnetic coupling between the two is maximized.

To function as a core for the external coil, the material used must have a relatively high magnetic permeability, at least greater than one. Although ferrite is commonly used for core materials, sintered powdered iron and other alloys can also be used. Since the magnetic characteristics of such materials are generally well understood by those of ordinary skill in the art, further details of the external coil and core need not be provided herein to provide an enabling disclosure of the present invention.

Housing 96 on external coil 90 provides RF shielding against electromagnetic interference (EMI). The housing for the external coil is preferably conductive, grounded, and surrounds the external coil except where the faces of the generally "C-shaped" core 94 are opposite the RF antenna. The RF shield comprising housing 96 is attached to an internal braided shield 99 of cable 98. Inside the power supply and patient monitoring console to which cable 98 is connected, shield 99 is connected to ground. The RF shield on the external coil, along with shields provided around transducers on the stent (not shown in this FIGURE) minimize external EMI radiation due to the use of the present invention within a patient's body.

For the embodiment shown in FIG. 7, external coil 96 is electromagnetically coupled to a spiral winding 108 in a stent 106 that is implanted in a blood vessel 107. Spiral winding 108 comprises the RF antenna for stent 106 and the opposite ends of the winding are coupled to an electronic circuit 110, which may comprise any of the circuits described above in connection with FIG. 1–6. Not shown in FIG. 7 are the one or more transducers that are included within the stent to monitor one or more parameters.

The RF antenna used in the stent may be either an integral part of the stent, or it may instead comprise a separate coil that is wound around or through the structure comprising the wall of the stent. To function within the body of a patient, a stent must be able to bend and flex with movement of the body, yet must have sufficient surface area and hoop strength to compress the atheriosclerotic material that is inside the blood vessel wall radially outward and support the vessel wall, maintaining the lumen cross section. Several manufacturers offer stent designs, each fabricated from wire, bent back and forth in a periodically repeating "S" shape or zigzag configuration, forming a generally cylindrical tube. Such stents are considered ideal for use in practicing the present invention, since the wire comprising the wall of the stent can be used for the RF antenna. Examples of such stents are the ANGIOSTENT made by AngioDynamics, the stent sold by Cordis Corporation, the CARDIOCOIL produced by Instent, and the WIKTOR stent from Medtronic Corporation.

Figure 8:
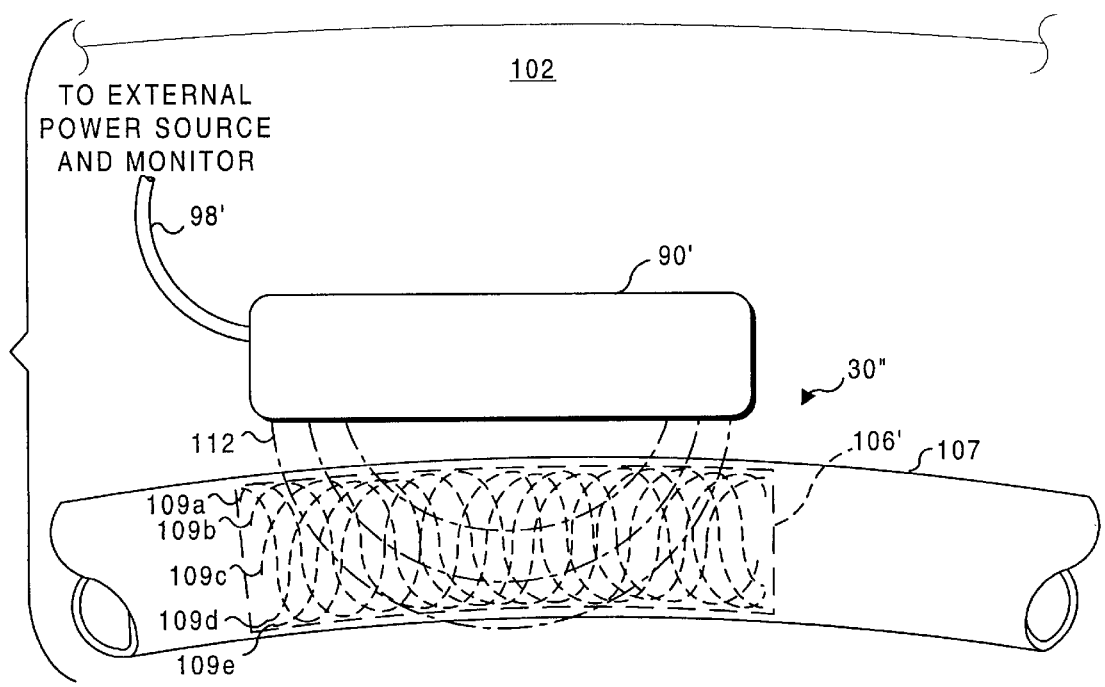
FIG. 8 is a cross-sectional view of an RF antenna in a stent implanted in a blood vessel, and includes a block that represents an implanted coil, which is electromagnetically coupled to the RF antenna.

FIG. 8 illustrates another embodiment in which an implanted coil 90' disposed outside blood vessel 107 adjacent to an implanted stent 106' is electromagnetically coupled through magnetic flux lines 112 to the stent using a plurality of electrically isolated and separate helical windings 109a, 109b, 109c, 109d, and 109e comprising the wall of the stent. Not shown are the electronic circuitry and transducers that are coupled to the windings comprising the RF antenna, however, it will be understood that any of the electronic circuits shown in FIGS. 1–6, discussed above, can be used for this purpose. However, by using electrically isolated and separate windings 109 for the RF antenna, it is possible to avoid multiplexing the signals from each different transducer used in the stent, since each transducer (or sets of transducers) can transmit data over its own winding and separately receive an excitation signal from implanted coil 90'. This figure shows the implanted coil coupled to an external power source and monitor through a cable 98'. Cable 98' can either penetrate the dermal layer of the patient's body, passing to the outside environment, or alternatively, may itself be electromagnetically coupled to an external coil, such as external coil 90 shown in FIG. 7. If the cable from implanted coil 90' penetrates the dermal layer, it is likely that the parameters being sensed by the stent will only need to be monitored for a relatively short time, so that the implanted coil can be removed from the patient's body after the need to monitor the parameters is satisfied. The advantage of the embodiment shown in FIG. 8 is that a stent implanted deep within a patient's body can be readily energized and the data that it provides can be more efficiently received outside the body by using implanted coil 90' as an interface, either directly coupled through the skin or electromagnetically coupled through the external coil.

Stents comprising a woven helical braid of fine wires are available from certain stent manufacturers. The braid provides the required hoop strength needed to support the wall of a blood vessel after the stent is implanted and expanded or allowed to expand. To maintain the required flexibility for the stent, the braided wires of such stents are not joined at the intersection points. An example of this type of stent is the WALLSTENT, which is sold by Medivent-Schneider. This configuration is also well-suited for practicing the present invention. To be used as the RF antenna, the wires forming the body or wall of the stent must be electrically insulated from the surrounding tissue of the blood vessel and must be insulated from each other where they cross except at any node wherein the helical turns are linked to form one or more sets of connected turns. The wire used for this configuration can be either round or flat.

Figure 9:
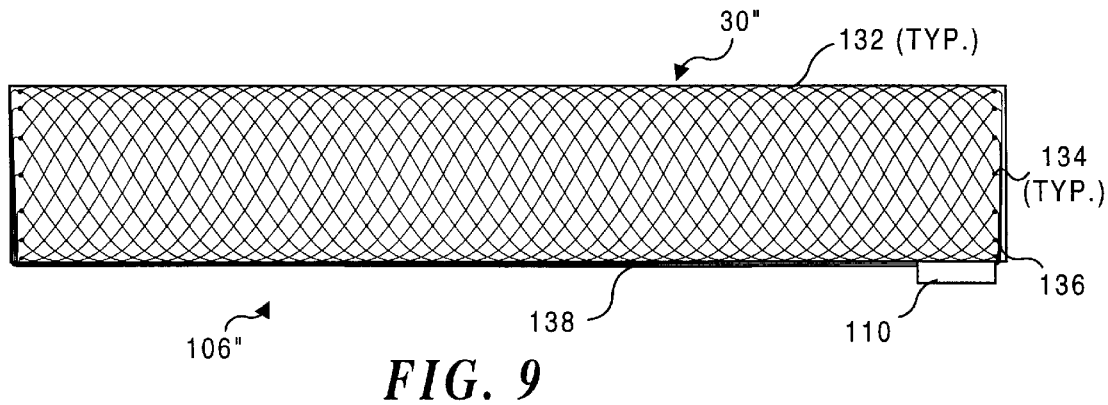
FIG. 9 is a side elevational view of a woven spiral mesh RF antenna that comprises a wall of a stent.

An embodiment of an RF antenna 30" comprising a stent 106" is shown in FIG. 9 to illustrate the configuration discussed above. RF antenna 30" comprises a woven mesh 132 fabricated from insulated wire so that overlapping segments of the mesh do not electrically connect in the center of the stent. At each end of the RF antenna, the wires comprising wire mesh 132 are electrically coupled together at nodes 134, producing a multi-turn coil. If each wire comprising the mesh passes around the central axis of the stent through m degrees, and if there are a total of n such wires, then the equivalent number of turns in RF antenna 30" is equal to n×m÷360. Leads 136 and 138 convey signals to and from nodes 134, connecting the wire mesh to electronics assembly 110.

The woven mesh structure of RF antenna 30" is often used for stents. However, it should be noted that currently available woven mesh stents are not woven from insulated wire, nor are the nodes of the mesh at each end electrically connected in commercially available stents. In the WALLSTENT by Medivent-Schneider, the ends are instead free floating. It is also contemplated that insulated electrical conductor could be woven into the structure of a commercially available mesh stent. Alternatively, the RF antenna coil could be fabricated from a woven mesh or from a plurality of spiral turns of a conductor and then the mechanical characteristics required of the stent could be achieved by providing an interwoven wire within the RF antenna. It is also noted that different electronic assemblies can be coupled to separate portions of the woven mesh RF antenna so that the different portions of the RF antenna and the electronic assemblies are electrically isolated from each other, or as a further alternative, the sections can be coupled in series.

Figure 10:
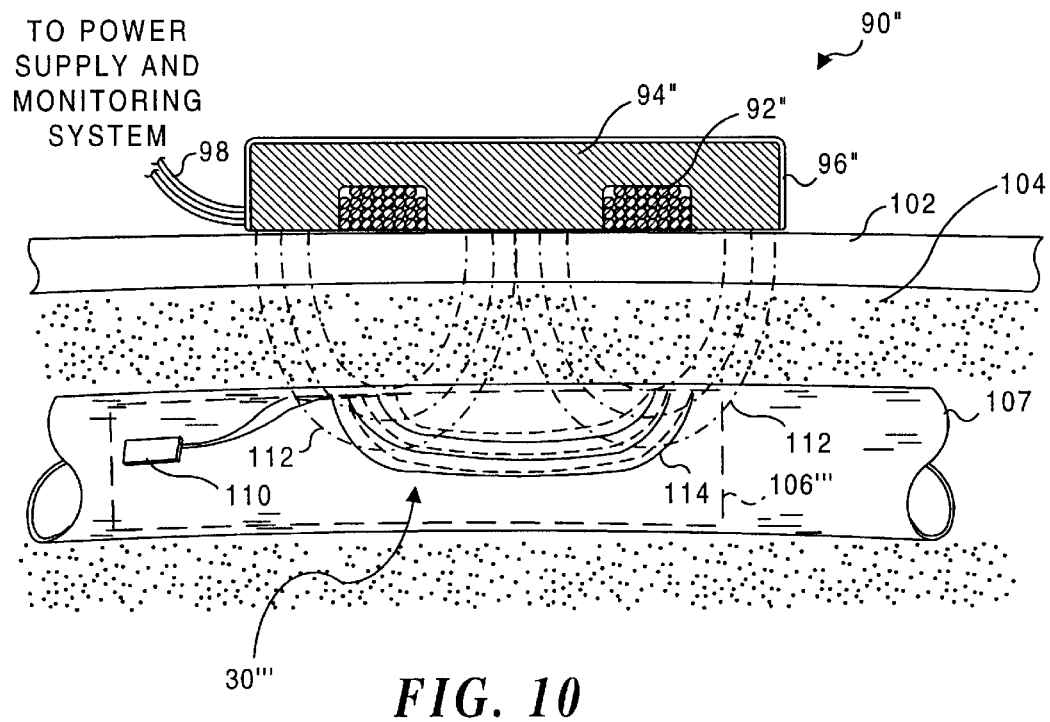
FIG. 10 is a cut-away side elevational view of a further embodiment of an external coil and a side elevational view of a blood vessel in which a stent is implanted that includes a saddle-shaped integrated RF antenna within the wall of the stent.

In FIG. 10, an RF antenna 30''' in a stent 106''' is illustrated that comprises a plurality of generally saddle-shaped coils 114 disposed within (or comprising) the wall of the stent. Again, the RF antenna is coupled to electronics assembly 110. Although only a single layer of saddle-shaped coils 114 is illustrated, it is contemplated that a plurality of such interconnected layers could be provided for the stent.

For use in electromagnetically coupling with RF antenna 30''' to energize the electronics assembly and to receive data from the transducers (not separately shown) on the stent, an external coil 90'' is provided that includes a plurality of coils 92'' wrapped around a central portion of a generally E-shaped core 94''. Lines of electromagnetic flux 112 are thus produced between the central leg and each of the end legs of core 94''. It will therefore be apparent that this embodiment of the RF antenna and of the external coil achieve optimum coupling when the distance separating the two is minimal. Therefore, RF antenna 30''' and external coil 90'' are best used in applications where stent 106''' is disposed relatively close to dermal layer 102 so that tissue 104 separating the stent from external coil 90'' is only a few centimeters thick. Maximal coupling is achieved when the longitudinal axis of external coil 90'' is aligned with the longitudinal axis of stent 106'''.

Figure 11A:
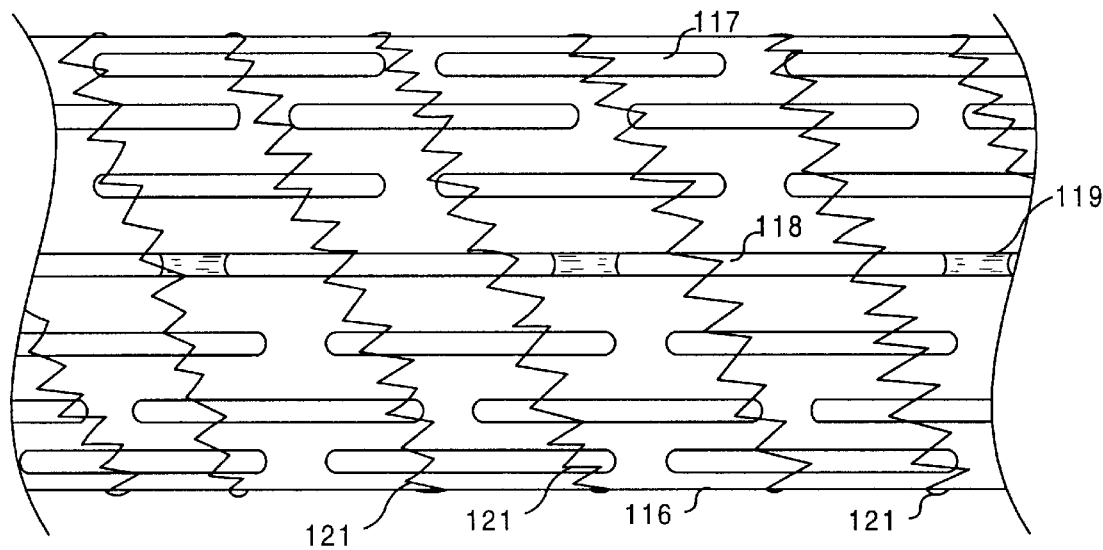
FIG. 11A is a side elevational view (showing only the foreground) of a portion of a metal tube-type stent with nonconductive weld joints, illustrating an RF antenna wrapped around the stent in a pre-expansion configuration.

FIG. 11A illustrates an embodiment of an RF antenna 121 that is helically coiled around the circumference of a stent fabricated by slotting a metal tube 116. The insulated conductor comprising the RF antenna is kinked (or fanfolded) when wound around metal tube 116 to accommodate expansion of the metal tube once implanted in a blood vessel. The insulation on RF antenna 121 prevents the turns from electrically shorting by contact with metal tube 116 or with surround tissue. Although not shown, the RF antenna will likely be adhesively attached to metal tube 116 at several spaced-apart locations. The ends of RF antenna 121 are coupled to one or more transducers or sensors (not shown) through an electronics assembly (also not shown) comprising any of the circuits shown in FIGS. 1–6.

Metal tube 116 includes a plurality of generally longitudinally extending slots 117 at spaced-apart locations around the circumference of the stent. These slots provide the expansibility and flexibility required of the stent. This design is similar to the Palmaz-Schatz stent made by Johnson & Johnson Corporation. To avoid providing a shorted turn with the body of metal tube 116, the generally conventional design of the stent is modified to include a break 118 in the metal tube circumference. The edges of metal tube 116 are connected at several joints 119 along the break using a non-conductive material.

Metal-to-ceramic (or metal-to-glass) welded joints are commonly employed in medical implants and other electrical devices. To minimize thermal stress in the joint, a material having a low coefficient of thermal expansion is typically used in the weld. For example, KOVAR, a nickel-iron allow (29% Ni, 17% Co, 0.3% Mn, and the balance Fe) is one material that can be used to form welded non-conductive joints 119 on metal tube 116. This material is commonly used to bond the lids onto ceramic chip carriers in the integrated circuit industry and thus is readily available.

Figure 11B:
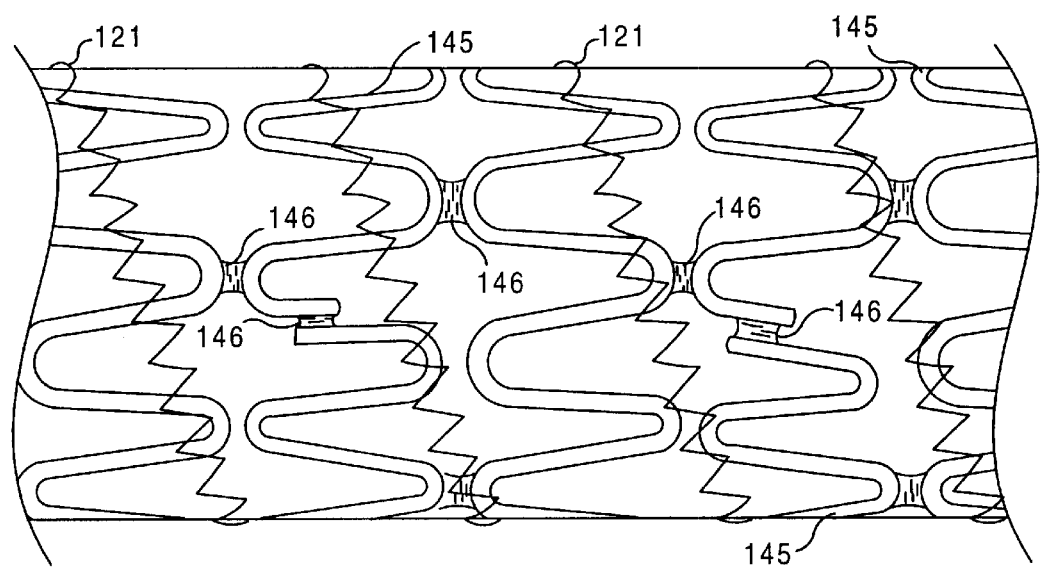
FIG. 11B is a side elevational view (showing only the foreground) of a portion of a zigzag wire stent with nonconductive joints, illustrating an RF antenna wrapped around the stent in a pre-expansion configuration.

An alternative design for a stent formed from a non-woven wire 145 about which RF antenna 121 is coiled is illustrated in FIG. 11B. The RF antenna is again formed of an insulated conductor that is helically coiled about the circumference of the stent. The body of the stent comprises a plurality of zigzag shapes formed of wire 145 that are joined by non-conductive welded joints 146 at spaced-apart points that prevent any shorted turns. This stent configuration is similar to that of the ACS RX MULTI-LINK stent made by Medtronic and the GFX (AVE) stent produced by Arterial Vascular Engineering.

Figure 12:
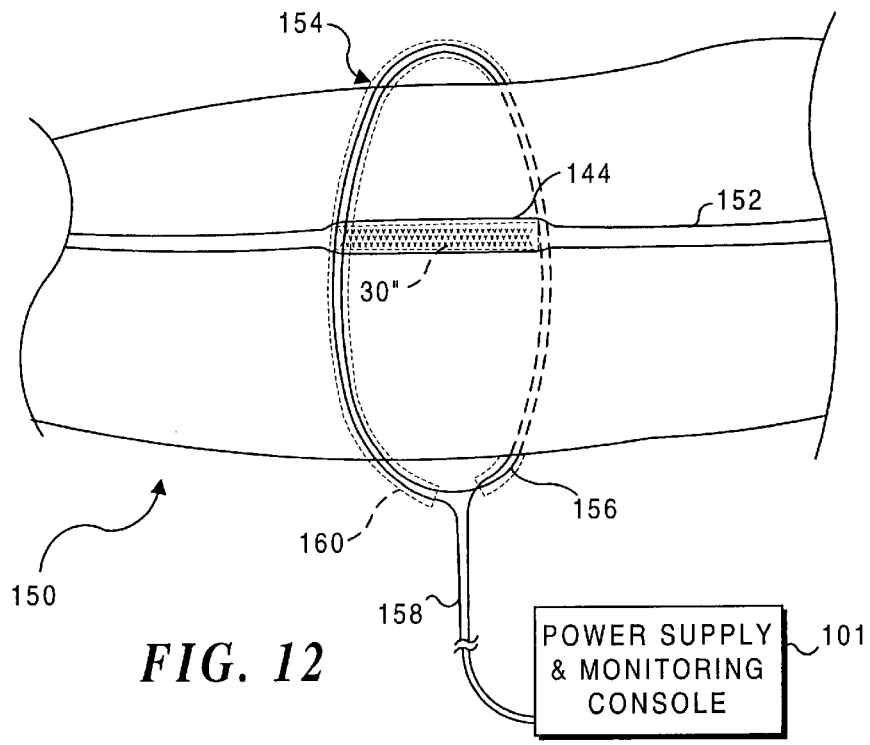
FIG. 12 is a cut-away view of a portion of a leg showing a stent implanted at a substantial depth within a blood vessel, and an external coupling coil that encompasses the stent.

In those cases where stents are implanted relatively deep inside the patient's body, at some distance from the surface of the patient's skin, an alternative external coil 154 can be employed, generally as shown in FIG. 12. In this example, a stent 144 comprising RF antenna 30'' is implanted within an artery 152, which is disposed within a thigh 150 of the patient. To couple with RF antenna 30'', external coil 154 includes a plurality of turns 156 sufficient in diameter to encompass thigh 150. An RF shield 160 encloses the outer extent of external coil 154, so that RF energy radiates only from the inner portion of turns 156. A lead 158 couples external coil 154 to a power supply and monitoring console 101. External coil 154 can be made sufficiently large to encompass the portion of the body in which the implanted stent is disposed such as the torso, another limb of the patient, or the neck of the patient. Coupling is maximized between external coil 154 and RF antenna 30'' (or other RF antenna) used on the stent when the central axes of both the RF antenna and the external coil are coaxially aligned and when the implanted stent is generally near the center of the external coil. Coupling between the RF antenna and the external coil decreases with increasing separation and begins to degrade when the implanted stent is more than one external coil radius away from the center point of the external coil. In addition, coupling is minimized when the central axes of the external coil is perpendicular to the axis of the RF antenna.

Description of the Ultrasonic Transducer Arrays

An ultrasonic transducer for monitoring flow or fluid velocity through a stent should be relatively compact included in or mounted on the wall of a stent. Typical prior art ultrasonic transducers include a planar slab of a piezoelectric material having conductive electrodes disposed on opposite sides thereof. Since such elements are planar, they do not conform to the circular cross-sectional shape of a stent. Moreover, prior art transducers are not compatible for use with a stent that is implanted within a patient's body and which is intended to be left in place for an extended period of time. Also, it is apparent that conventional ultrasonic transducer elements will not readily yield to being deformed into a compact state for implacement within a blood vessel, followed by expansion of a stent body to apply radially outwardly directed force to compress the deposits within a blood vessel.

Figure 13:
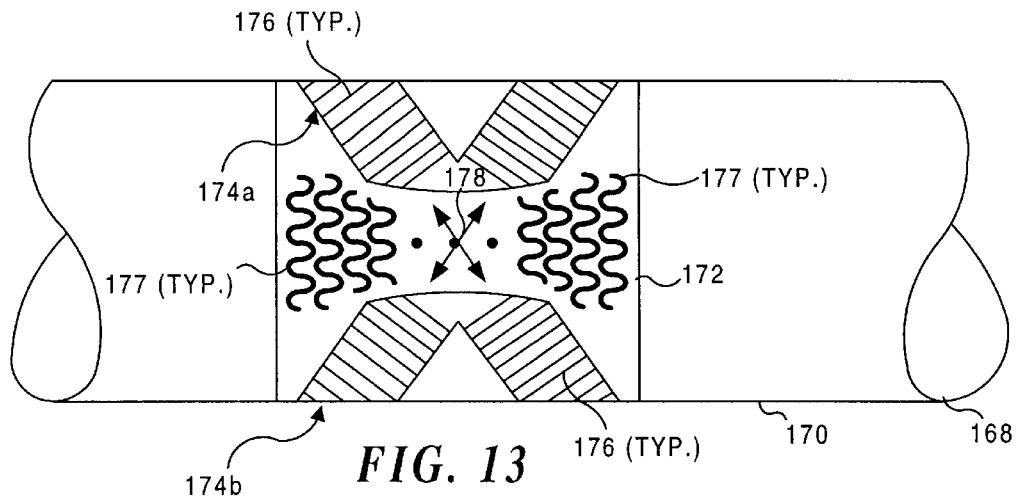
FIG. 13 is a side elevational schematic view of a dual beam conformal array transducer on an expandable carrier band for use in a stent.
Figure 14:
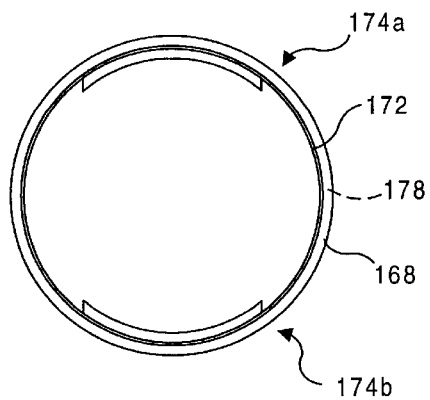
FIG. 14 is an end elevational view of the conformal array transducer of FIG. 13, within a stent.
Figure 15:
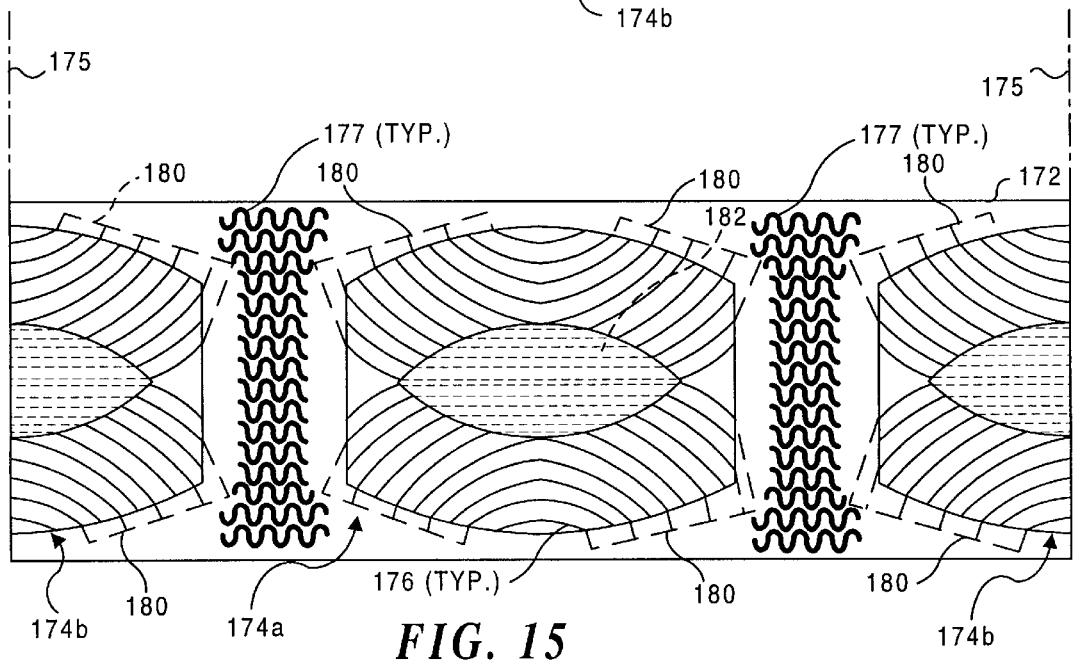
FIG. 15 is a plan view of the conformal array transducer shown in FIGS. 13 and 14, cut along a cut line to display the dual conformal arrays in a flat disposition.

FIGS. 13–15 show an embodiment of an extremely low profile ultrasonic transducer comprising conformal arrays 174a and 174b, which are disposed on opposite sides of a stent 168. Since it is contemplated that this type of ultrasonic transducer assembly might be used on several different designs of stents, details of stent 168 are not illustrated. Instead, only a portion of its outline 170 is shown. Ideally, each conformal array comprises a piezoelectric plastic used as a transduction material and having sufficient flexibility to allow the transducer elements to conform to the circular cross section of the wall of stent 168 when the stent is inserted through the patient's vascular system and to flex as the stent is expanded within a blood vessel. Such flexible piezoelectric plastic materials are readily available.

When used for transit time measurements, as shown in FIGS. 13 and 14, conformal arrays 174a and 174b are disposed generally on opposite sides of the blood vessel and encompass much of the inner circumference of the vessel. However, when a pulsed Doppler measurement is made using the conformal array transducer, only a single such transducer is required, since the transducer first produces an ultrasonic wave that is transmitted into the lumen of the stent and then receives an echo reflected back from the fluid flowing through the stent. If used for continuous wave (CW) Doppler measurements, the pair of conformal array transducers disposed on opposite sides of the stent are again needed, one transducer serving as a transmitter and the other as a receiver. In each case, it is presumed that the fluid has a non-zero flow velocity component directed along an ultrasonic beam axis of the ultrasonic wave produced by the conformal array transducer serving as a transmitter.

Conformal arrays 174a and 174b shown in FIGS. 13–15 produce ultrasonic beams 178 that are tilted relative to the transverse direction across the stent in substantially equal but opposite angles with respect to the longitudinal axis of the stent. Since dual beam transit time measurements are implemented by conformal arrays 174a and 174b, the results are self-compensating for tilt angle errors. This form of self-compensation is only required where the alignment of the conformal array relative to the longitudinal axis of the stent may be imperfect. For transit time measurements made on stents wherein the alignment of the transducer relative to the longitudinal axis of the stent remains accurately known, an opposed pair of conformal arrays disposed on opposite sides of the vessel is sufficient so that the added complexity of the dual beam transducer geometry is not required for self compensation.

In the case of pulsed Doppler velocity measurements, a single transducer would again likely be adequate so long as the alignment of the transducer to the stent is accurately controlled. If the alignment of the conformal array transducer is not controlled or not well known, a second such transducer can be used to gather velocity data along a second beam axis using pulsed Doppler velocity measurements. Assuming that the second axis is tilted in an equal but opposite direction as the first axis, the Doppler measurements made by the two conformal array transducers should be self-compensating for tilt errors. In this case, the second conformal array transducer could be mounted on the same or on an opposite side of the stent from that where the first conformal array transducer is mounted to implement the Doppler measurements.

For CW or pseudo-CW Doppler velocity measurements (in which a relatively long duration pulse of ultrasonic waves is produced), the transit signal is applied for a sufficiently long period so that a second transducer is needed to receive the echo signals. In this case, a single set of diametrically opposed conformal array transducers can be used.

As perhaps best illustrated in FIG. 14, conformal array transducers 174a and 174b need not wrap entirely around the stent. In the illustrated embodiment, the conformal array transducers each span an arc of approximately 60° around the longitudinal axis of the vessel (i.e., about the center of the circular vessel as shown in FIG. 14). This geometry produces a measurement zone through which ultrasonic beams 178 propagate that is nominally equal to about 50% of the vessel outer diameter. If used for Doppler velocity measurements, it is contemplated that the conformal array transducer need cover only a central portion of the stent. As a result, the span of the conformal array transducer can be reduced from about 60° to about 45°.

To produce a wide, uniform ultrasonic beam such as that needed for transit time measurements of flow, the conformal array transducer must produce ultrasonic waves having a wave front characterized by a substantially uniform amplitude and phase. As shown in FIG. 13, lateral projections through each of a plurality of transducer elements comprising the conformal array transducers are indicated by straight lines 176. These straight lines indicate the centers of the transducer elements and are perpendicular to the axis of propagation of waves 178 (represented by bi-directional arrows directed along the axes of propagation of the ultrasonic waves). In the preferred embodiment, the spacing between the element centers, i.e., between straight lines 176, is approximately equal to a phase angle of 90° at the transducer's excitation frequency. Thus, starting at the top of FIG. 13 and working downwardly, transducer elements disposed along each of the displayed straight lines produce acoustic waves that are successively delayed by 90°, or one-quarter wavelength in the fluid medium through which the ultrasonic waves propagate. For tissue, a sound velocity of 1,540 meters/second is normally assumed, so that the physical spacing of the projected straight lines would typically be defined by the following:

Projected Spacing in millimeters=$1.54/(4*F_0)$ where $F_0$ is equal to the center frequency in MHz. If zero degrees is assigned to the top-most element of conformal array 174a, the next element would operate at −90° relative to the top element, followed by an element operating at −180°, and then one operating at −270°, and finally by an element operating at 0° relative to the top electrode. Thus, conformal array 174a produces a succession of ultrasonic waves spaced apart by a 90° space shift, thereby achieving a desired phase uniformity across the transducer.

Amplitude uniformity can be achieved in the ultrasonic wave front by "shaving" the elements of the conformal array. Although shaving could be achieved in a variety of ways, the preferred embodiment controls shaving by varying the area of each element.

Conformal array transducers 174a and 174b are carried on a band 172 preferably made from the piezoelectric plastic material used for the element substrate, which is sized to fit snugly around an outer surface of the stent or inserted into the lumen of the stent (as shown in FIG. 14). Band 172 is intended to position the conformal array transducers in acoustic contact with stent wall 168, if the band is wrapped around the stent, or to maintain the conformal array transducer against the inner surface of the stent, if the band is inserted into the lumen of the stent. Contact of the band around the outer surface of the stent assures that the ultrasonic waves produced by the element of the conformal array are conveyed into the fluid flowing through the interior of the lumen. Preferably, the piezoelectric plastic comprising band 172 is fabricated from a material such as polyvinylidene fluoride (PVDF), poly(vinyl cyanide-vinyl acetate) copolymer (P(VCN/VAc), or poly(vinylidene fluoride-trifluoroethylene) copolymer (P(VDF-TrFE)). Preferably, P(VDF-TrFE) is used because of its superior piezoelectric coupling and relatively lower losses.

Referring now to FIG. 15, further details of the conformal array transducers are illustrated. In this embodiment, alternating elements of the conformal array produce ultrasonic waves differing by 90°. In the view shown in FIG. 15, a cut line 175 intersects the lateral center of conformal array 174b. In practice, any cut would more likely extend through band 172 at a point approximately midway between conformal array 174a and conformal array 174b. Electrodes comprising each element of the conformal array can be photolithographically generated on the piezoelectric plastic substrate comprising band 172. Alternatively, the elements can be formed on a non-piezoelectric material comprising band 172, and then the material with the elements formed thereon can be bonded to a piezoelectric substrate in each area where a conformal array transducer element is disposed. In this latter embodiment, it is contemplated that a flex circuit material such as a polyimide could be employed for band 172, and that conventional photolithographic processing methods might be used to fabricate the conformal array transducer circuitry on the band. Further, the centers of alternating conformal array elements are coupled together electrically via conductors 180 (shown as dash lines) in FIG. 15. Not shown in FIGS. 13–15 are the leads that extend from an electronics assembly used to drive the conformal array. Any of the electronic circuits shown in FIGS. 1–5 could be used for the electronics assembly.

The pattern of elements comprising each of the conformal array transducers and the boundary of each conformal array (top and bottom as shown in FIG. 15), define sinusoidal segments. The period of the sine wave from which these sinusoidal segments are derived is approximately equal to the circumference of band 172. Further, the amplitude of that sine wave generally depends on the desired beam angle relative to the longitudinal axis of the stent. For the sinusoidal segment employed for each electrode, the amplitude is defined by:

$$\text{Amplitude} = D * \tan \Theta$$

Similarly, the amplitude of the sinusoidal segment defining the boundary of each conformal array is defined by:

$$\text{Amplitude} = D/(\tan \Theta)$$

where $\Theta$ is equal to the angle between the longitudinal axis of the stent and the ultrasound beam axis and D is equal to the external diameter of the stent. Accordingly, it should be apparent that one sinusoidal template could be used to draw all of the transducer elements and a second sinusoidal template (differing only in amplitude from the first) could be used to draw the boundary of each conformal array transducer. The transducer elements are displaced or spaced apart from one another as required to achieve the phase relationship described above in connection with FIG. 13. In addition, the actual physical electrode pattern and placement of the elements on band 172 can be determined by finding intersection loci between band 172 as wrapped around (or within the inner circumference of) the stent and equally-spaced planes. The spacing between these planes is defined by the equation noted above for the projected spacing.

Conductors 180 that connect transducer elements of the same phase differ by 90°. There are two ways to achieve the 90° phase variation between the ultrasonic waves produced by successive electrodes in the conformal array. In the first approach, a uniformly polarized piezoelectric plastic substrate is used and every fourth element is connected together, producing four groups of elements or electrodes that produce ultrasonic waves having phasal relationships of 0°, 90°, 180°, and 270°, respectively. Alternatively, a zone polarized piezoelectric plastic substrate could be used and every other element can be connected together (as shown in FIG. 15). Each of these two groups is then connected to provide an in phase and a quadrature phase transceiving system, so that ultrasonic waves are produced by the elements having a relative phase relationship of 0° and 90°. In the first approach, a multi-layer interconnect pattern is required to connect to all traces for each of the transducer elements in the four groups. In addition, a more complex four-phase electronic driving system that includes a phase shifter is required. Specifically, the signal applied to each of the four groups must differ by 90° between successive elements to achieve the 0°, 90°, 180°, and 270° driving signals. The phase shifter, e.g., included in the modulator that drives the transducer, provides the phase shifted excitation signals applied to each successive element of the transducer.

In the second approach, which is preferred because it simplifies the electronic package required and because it facilitates use of a simpler, double-sided electrode pattern, the piezoelectric plastic material must be locally polarized in a specific direction, depending upon the desired phase of the electrode at that location. A polarity reversal provides a 180° phase shift, eliminating the need for 180° and 270° electronic signals. Thus, the zones of the substrate designated as 0 and 90° would be connected to the signal source with the poles of the elements in one direction, while zones for elements designated to provide a relative phase shift of 180° and 270° would be connected with the poles of the elements in the opposite direction. Elements producing ultrasonic waves with a relative phase relationship of 0° and 180° would comprise one group, and elements producing ultrasonic waves with a relative phase relationship of 90° and 270° would comprise a second group. Connecting the poles of the different groups in local regions in opposite directions is achieved by applying electric fields of opposite polarity in those areas during manufacture of the conformal array transducer. The final element wiring pattern required to actually energize the conformal array transducer when it is employed for monitoring flow and/or velocity of fluid through the vessel would preclude applying electric fields in opposite polarity. Accordingly, the required poling relationship would have to be performed using either temporary electrodes or by providing temporary breaks in the actual electrode pattern employed in the final conformal array transducer.

In the preferred embodiment, to achieve a desired frequency of operation, it is contemplated that the electrode mass would be increased to a point well beyond that required for making electrical connections. This added mass would act together with the piezoelectric plastic material to form a physically resonant system at a desired frequency. In this manner, a relatively thinner and more flexible piezoelectric plastic material can be used for the substrate comprising band 172. Use of mass loading in this manner is well known to those of ordinary skill in the art of transducer design, at least in connection with producing large, single element, piston transducers.

Figure 17:
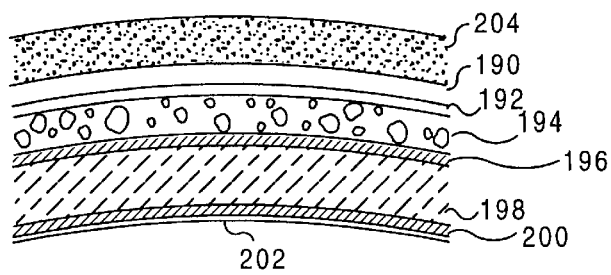
FIG. 17 is an enlarged partial transverse cross-sectional view of the layers comprising the conformal array transducer disposed on a stent within a blood vessel.

The conformal array transducers can be formed on band 172, but alternatively, can be included within the structure of a stent, i.e., within its wall. FIG. 17 illustrates a portion of a cross-sectional view of the conformal array transducer fabricated in the stent. The entire transducer assembly is fitted within a stent body 190. Details of the stent body are not illustrated, since it is contemplated that many different types of stent configurations are suitable for carrying the conformal array transducer. Stent body 190 is shown inside a blood vessel wall 204. A biocompatible outer coating 192 comprises the next layer, protecting the conformal array transducer from contact with bodily fluids. Below the outer coating is an acoustic backing 194 comprising a conventional, or a syntactic foam, i.e., a polymer loaded with hollow microspheres, such as is well known to those of ordinary skill in the art, serves both for acoustic isolation and dampening and to minimize capacitive loading. The acoustic backing has a relatively low dielectric constant, thereby minimizing capacitive loading between the electrodes and surrounding tissue. Acoustic backing 194 thus insulates the transducer elements from the surrounding fluid and tissue in a capacitive sense, and also in an acoustic sense. The next layer radially closer to the longitudinal center of the vessel comprises a rear electrode 196. A front electrode 200 is spaced apart from the rear electrode by a piezoelectric plastic layer 198. As noted above, in the preferred embodiment illustrated in FIGS. 13–15, piezoelectric plastic layer 198 comprises band 172. Piezoelectric layer 198 (or band 172) has a relatively low dielectric constant, e.g., from about six to eight) compared to tissue (approximately 80).

Rear electrode 196 and front electrode 200 preferably comprise multi-layer structures (although separate layers are not shown). For example, the electrodes will include a metallic layer that bonds well to the piezoelectric plastic material, for example, titanium, followed by a highly conductive layer, for example, copper, followed by an oxidation resistant layer, for example, gold. Such multi-layer systems are well known in the field of electronic interconnects and are ideally suited for use as electrodes in the conformal array transducer. Preferably, front electrode 200 is the "common electrode" for the transducer elements and serves as an RF shield. A front coating 202 serves as an acoustic coupling between the conformal array transducer and the fluid in the lumen of the stent. In addition, the front coating layer serves as a biocompatible layer, providing a barrier to fluid ingress into the conformal array transducer.

In both the conformal array transducer assembly provided in band 172 (as shown in FIGS. 13–15) and the transducer assembly included within the structure of the stent wall, as illustrated in FIG. 17, it is contemplated that adhesive layers (not shown) may be used between the various layers. However, certain layers such as front and rear electrodes 200 and 196 will likely need not be adhesively coupled to the piezoelectric material if photolithographically formed on the material. Other layers may not require an adhesive to couple to adjacent layers, e.g., if formed of a thermoset material that self bonds to an adjacent layer when set.

Figure 18:
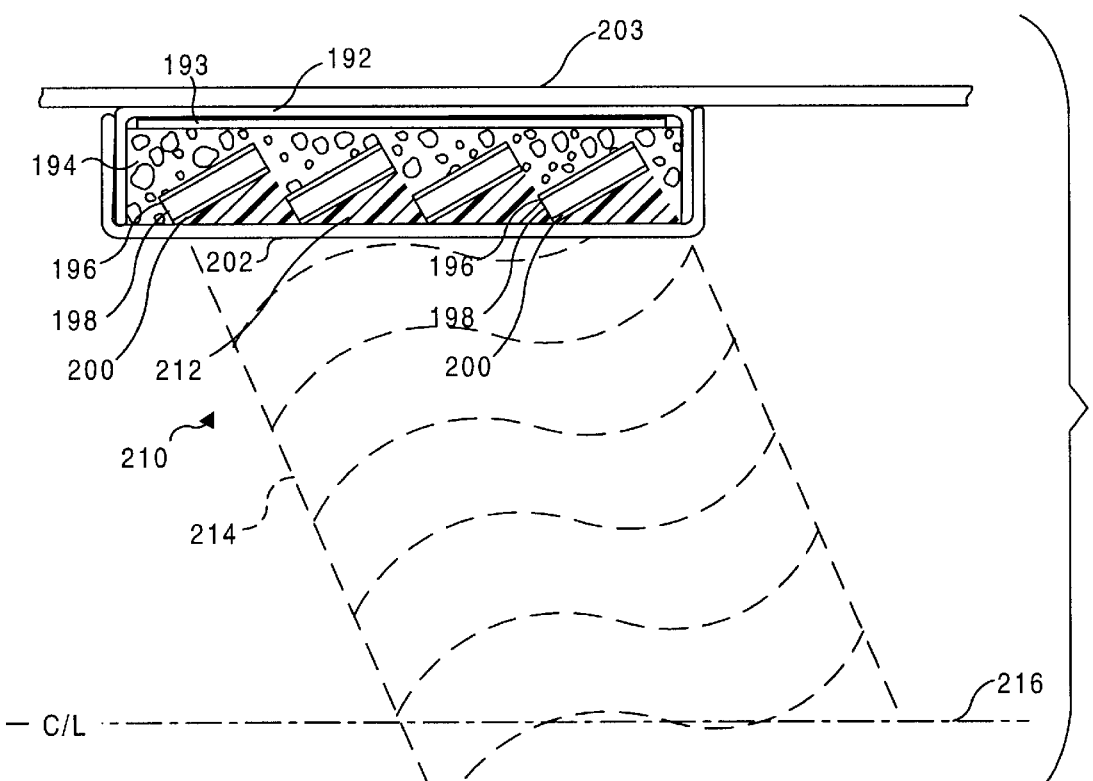
FIG. 18 is an enlarged partial cross-sectional side view of a tilted-element transducer array disposed within a stent.

As noted above, one of the advantages of the conformal array transducer is its relatively low profile. In some cases, a stent may integrally accommodate a relatively thicker profile transducer assembly. An embodiment of a tilted element transducer 210 is illustrated in FIG. 18. Each element comprising tilted element transducer 210 includes rear electrode 196 and front electrode 200 disposed on opposite sides of piezoelectric material 198. Conventional prior art transducers for producing an ultrasonic waves use a single such element that has a substantially greater width that is too great for inclusion within a stent assembly. In contrast, tilted element transducer 210 includes a plurality of elements like those shown in FIG. 18 that minimize the radial height (or thickness) of the transducer.

The tilted element transducer is disposed within the body of a stent 203, generally as shown in FIG. 18. Outer coating 192 again serves the function of providing a biocompatible layer to protect the transducer components contained therein from exposure to bodily fluids. RF shield 193 extends over the tilted elements, immediately inside outer coating 190. Below RF shield 193 is disposed acoustic backing 194.

An acoustic filler material 212 is disposed between front electrode 200 and front coating 202, on the interior surface of the stent, and is used to fill in the cavities in front of the transducer elements. The acoustic filler material is characterized by a relatively low ultrasonic attenuation, so that it readily conveys the ultrasonic waves produced by the elements into the lumen of the stent. In order to minimize reverberations of the ultrasonic waves in this acoustic filler material, its acoustic impedance, which is equal to sound velocity times density, is approximately equal to that of the fluid in the vessel. The velocity of sound in the acoustic filler material should also be close to that of the fluid flowing through the stent so that the sound beam is not significantly deflected by the acoustic filler material. Alternatively, an acoustic filler material having a relatively low sound velocity compared to the fluid may be used. In this case, the acoustic filler material acts as an acoustic lens that deflects the sound being produced by the tilted transducer elements, for example, materials such as silicones or fluorosilicones, typically having sound velocities about 1000 meters per second (compared to a sound velocity of approximately 1540 meters per second for blood), may be used. Low velocity lenses are generally well known in the art of ultrasonic transducers. The benefit of using a low velocity acoustic filler material is that the tilted transducer elements can be tilted about 30% less than would be required otherwise. As a result, the overall height of the tilted element transducer portion of the stent can be made about 30% thinner than would be possible without the low velocity acoustic filler material. In combination, the plurality of tilted elements produce an ultrasonic wave 214 that propagates at an angle relative to the longitudinal axis of the stent, which is represented by a center line 216 in FIG. 18.

Figure 16A:
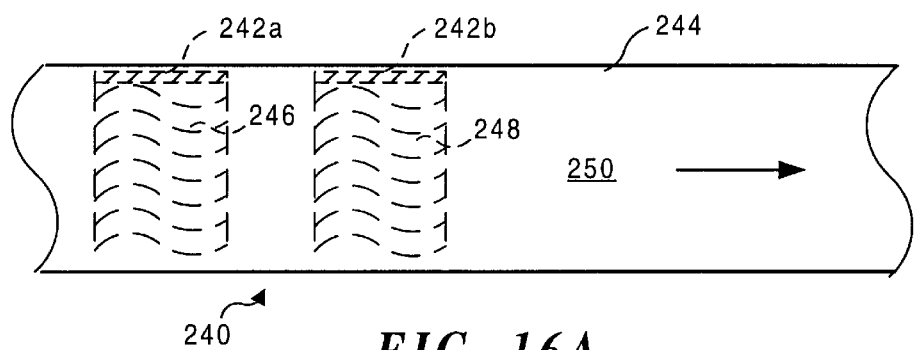
FIG. 16A is a cross-sectional side view of a portion of a stent in which are disposed transversely oriented transducers for monitoring flow using correlation measurements.
Figure 16B:
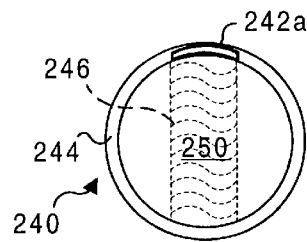
FIG. 16B is a transverse cross-sectional view of the stent and transversely oriented transducers shown in FIG. 16A.

In FIGS. 16A and 16B, an alternative approach for monitoring the velocity of a fluid through an interior 250 of a stent 240 is illustrated. In this embodiment, a pair of ultrasonic transducers 242a and 242b are mounted in relatively close proximity within a body 244 of stent 240. Ultrasonic transducers 242a and 242b each produce a pulse and receive the echo back from fluid flowing through interior 250 of the stent, the echoes being scattered from the fluid flowing therein. In this embodiment, the signals received from transducer 242a in response to the echo is correlated with the similar signal from ultrasonic transducer 242b, resulting in a time delay estimate. The velocity of the fluid is then computed by dividing a distance between the center of transducer 242a and the center of transducer 242b by the time delay that was determined from the correlation analysis.

Unlike a Doppler system, the echoes in a correlation type transducer system like that shown in FIGS. 16A and 16B are not frequency shifted. Instead, the velocity signal is extracted by correlating the echo amplitude versus time signals for a pair of range bins. The velocity versus time is independently determined for each range bin, resulting in a time dependent velocity profile across the diameter of the stent.

Figure 19:
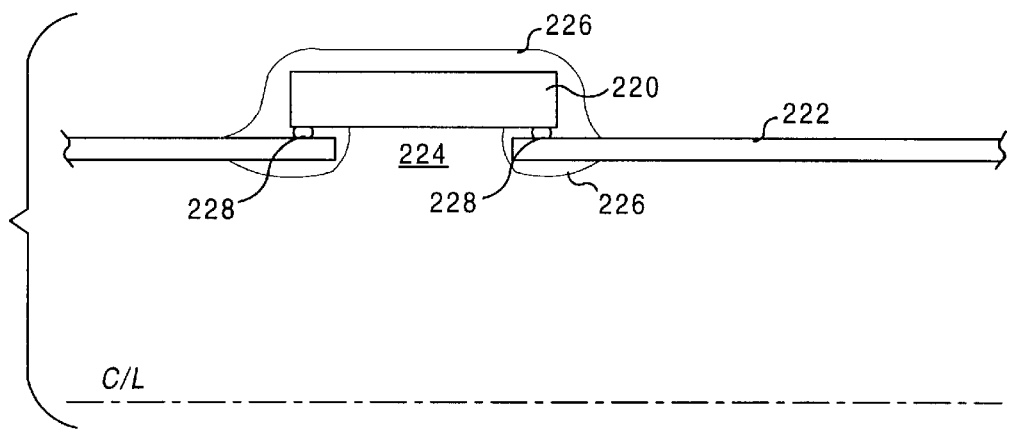
FIG. 19 is an enlarged partial cross-sectional side view of an integrated circuit (IC) transducer mounted on a stent.

FIG. 19 illustrates an integrated circuit (IC) sensor 220 mounted on a stent body 222, so that the IC sensor overlies a sensor window opening 224 in the stent body. Conductive adhesive or solder drops 228 couple the IC sensor contacts to the stent body (or to conductors that are coupled to one of the electronic assemblies shown in FIGS. 1–6). A biocompatible coating 226 encloses the IC sensor, except in the area of the sensor window opening through which the IC sensor is in contact with the fluid flowing through the lumen of the stent. It is contemplated that the IC sensor might be used for measuring parameters such as pressure, temperature, blood gas concentration, and insulin level or the levels of other metabolite such as glucose or sodium in the blood stream of a patient in which a stent that includes the IC sensor is implanted. As explained above, the IC sensor is electrically energized with electrical power that is electromagnetically coupled to the RF antenna that comprises the stent body or which is incorporated as one or more separate insulated windings within the stent wall structure. Signals produce by the IC sensor are converted to data signals, which are electromagnetically coupled to a monitor outside the patient's body, also as explained above. In certain applications of IC sensors, it may be advantageous to perform a differential measurement between two spaced-apart locations on the stent. Thus, to monitor fluid flow through the lumen of a stent, a differential pressure measurement made by transducers respectively disposed adjacent the proximal and distal ends of the stent provide and indication of the flow and of any blockage with the lumen of the stent.

If an external source of heat is applied to heat the blood or other fluid flowing through the lumen of a stent, flow can be determined by monitoring the temperature of the fluid with an IC sensor response to that parameter. An external source of RF energy electromagnetically coupled into the stent body, as disclosed above, can both provide the electrical power for the components of the stent sensor system and provide the power for heating the fluid. To avoid tissue damage, the maximum stent temperature should remain below 42.5° C., which is well established as the temperature above which hyperthermia and irreversible damage to tissue occurs. By analyzing the resultant temperature vs. time "thermal washout" curve, the flow rate of fluid through the stent can be determined. A differential temperature measurement made by temperature sensors disposed adjacent the opposite ends of a stent could also be used to determine flow through the stent lumen. Using the signals from these sensors, two temperature vs. time curves can be developed simultaneously. Differences in the observed thermal washout curves should be primarily a function of flow through the lumen and thus indicative of that parameter.

Other methods can be employed to determine flow based on temperature measurements. For example, by modulating the RF power used to heat the stent, the temperature vs. time curves will exhibit the modulation frequency. The temperature vs. time curves produced by spaced-apart temperature sensors can be filtered with a relatively narrow bandwidth filter, and the phase of the two filtered signals compared to extract a flow velocity through the stent. The signal processing concept of this approach is conceptually similar to that used for measuring cardiac output using a catheter-mounted heater and temperature sensors, as disclosed in U.S. Pat. No. 5,277,191 (T. J. Hughes).

Several types of IC sensors that might be incorporated within a stent in accord with the present invention are disclosed in previously issued U.S. patents. For example, U.S. Pat. Nos. 4,020,830 and 4,218,298 describe chemical field effect transistor (FET) transducers that are sensitive to specific chemical substances or to their properties. U.S. Pat. No. 5,552,272 describes a device for detecting the presence of an analyte of interest by generating a fluorescent signal when an attachment layer is exposed to a specific group of chemical substances. U.S. Pat. No. 4,935,345 discloses an implantable microelectronic biochemical sensor that incorporates a thin film themopile for use in monitoring concentrations of glucose or other chemicals present in the blood stream.

Other prior art devices are potential candidates for use as an IC sensor on a stent. In a paper entitled "Evaluation of a Novel Point-of-Care System, the I-Stat Portable Clinical Analyzer, CLINICAL CHEMISTRY, Vol. 39, No. 2, 1993, K. A. Erickson et al. describe a blood analyzer based on disposable IC biosensors that can quantify sodium, potassium, chloride, urea, nitrogen, and glucose levels. A good overview of acoustic wave biosensors is provided by J. C. Andle et al. in an article by that title published in the Proc. 1995 IEEE Ultrasonics Symposium, pp. 451–460. Other types of IC biosensors are described in the art. However, the present invention is not directed to details of such IC sensors. It is sufficient for this disclosure to recognize that such IC sensors are well known in the art and are generally available or readily fabricated for use on a stent as described above.

Figure 20:
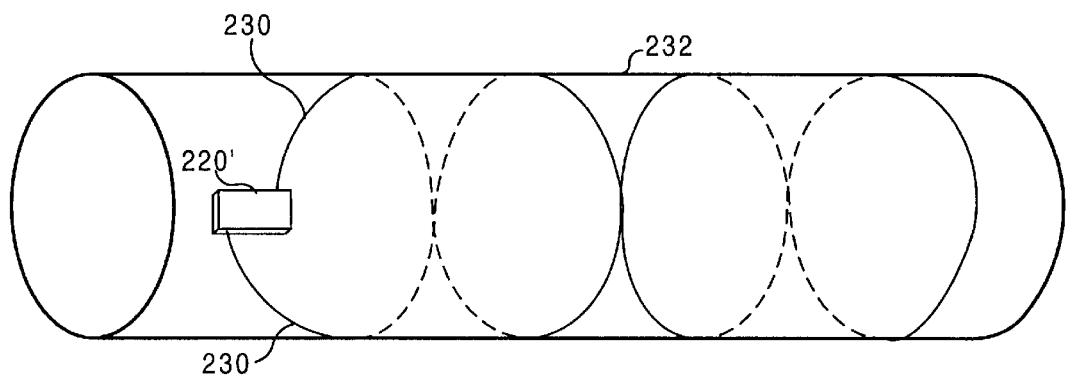
FIG. 20 is a side elevational schematic view showing an IC strain sensor and sensing filaments disposed on a stent.

A stent may include other types of sensors beside the ultrasonic transducers and IC sensor noted above. FIG. 20 illustrates an outline of a stent 232 that includes a strain sensor mounted on the stent. In the disclosed embodiment, strain sensing filaments 230 are wound around the stent body to measure displacement that is sensed by an IC sensor 220'. Filaments 230 exhibit a change in electrical resistance with strain and are therefore usable to sense the strain experienced by the stent when it is expanded inside a blood vessel. It is contemplated that filaments 230 be used only for strain sensing, so that their dimension, disposition, and metallurgy can be optimized for that function. Alternatively, the filaments can comprise part of the structural body of the stent so that they also provide a mechanical function related to the conventional function of a stent. It is also contemplated that strain gauges (not separately shown) can be used instead of filaments 230. The strain gauges can be mounted to a stent body at selected spaced-apart locations to measure displacement. Metallized polyimide substrate strain gauges should work well in this application, by wrapping the substrates around the body of the stent and attaching the substrate to the body at selected spaced-apart points. By monitoring the size of a stent as it is expanded, strain gauges or other strain measuring sensors can determine when a desired extension of the stent has been achieved. Alternatively, the strain data can be employed to assess the elasticity of the stent and blood vessel structure by monitoring the dynamic strain over cardiac cycles, i.e., with successive systolic and diastolic pressure levels.

Figure 21B:
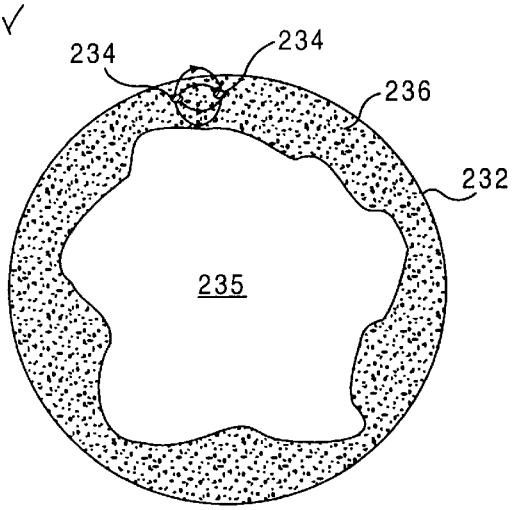
FIG. 21B is a cross-sectional view of a lumen of the stent in FIG. 21A, illustrating fatty tissue ingrowth.
Figure 21A:
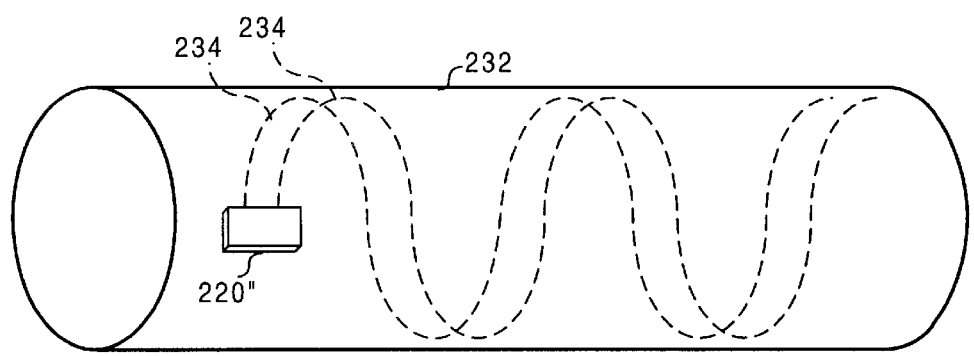
FIG. 21A is side elevational schematic view of a stent outline showing a deposit and ingrowth IC sensor and sensing filament.

Referring to FIG. 21A, an IC sensor 220" that detects fatty deposits and tissue growth inside the lumen of the stent is illustrated on stent body outline 232, connected to a pair of dielectric sensing filaments 234. IC sensor 220" detects fatty deposits and tissue ingrowth within the lumen of the stent by measuring the dielectric properties of any material in contact with dielectric sensing filaments 234, which are helically coiled around the inner surface of the stent body, from about one end of the stent to its opposite longitudinal end. Alternatively, dielectric sensing filaments 234 can be incorporated into the body or wall of the stent itself. For example, in a stent fabricated with a woven mesh, a portion of the mesh can be utilized for making the dielectric measurement, while the remainder is used for the RF antenna.

For measuring the dielectric properties, IC sensor 220" is energized with power electromagnetically coupled from an external source into the RF antenna of the stent and produces signals indicative of the fatty ingrowth that are electromagnetically coupled to the external monitoring system through the RF antenna of the stent. An RF signal at a frequency of from 10 to 100 MHz is applied to the dielectric sensing filaments. At such frequencies, tissue has the properties shown in the following Table 1. FIG. 21B illustrates an exemplary cross section of a lumen 235 within stent body outline 232, showing the ingrowth of a fatty tissue 236, which is in contact with the dielectric sensing filaments 234.

TABLE 1

| Tissue Type | Relative Permittivity | Resistivity (Ohm-cm) |
| --- | --- | --- |
| Fat | 6 to 20 | 2000 to 3000 |
| Blood | 80 to 160 | 80 to 90 |
| Muscle | 60 to 130 | 100 to 150 |

The permittivity of tissue is closely related to its water content, and water has a relative permittivity of about 80. Since fat and fatty deposits of the type found inside blood vessels contain much less water than other tissue types, the permittivity of fat is much lower than that of muscle or blood. The wall of a blood vessel is muscular and highly perfused and will therefore have a much higher permittivity than a fatty deposit. Similarly, fatty deposits have a much higher resistivity than either blood or muscle. Therefore, a measurement of the dielectric properties of tissue inside a stent can differentiate a fatty deposit from either blood or muscular tissue ingrowth into the lumen. The measurement can include a determination of capacitance, resistance, or a combination of the two.

Further information can be obtained from the frequency dependence of the capacitance and resistance measured inside a stent lumen. For example, blood has a relatively flat resistivity vs. frequency characteristic curve, compared to that of muscle.

Figure 22:
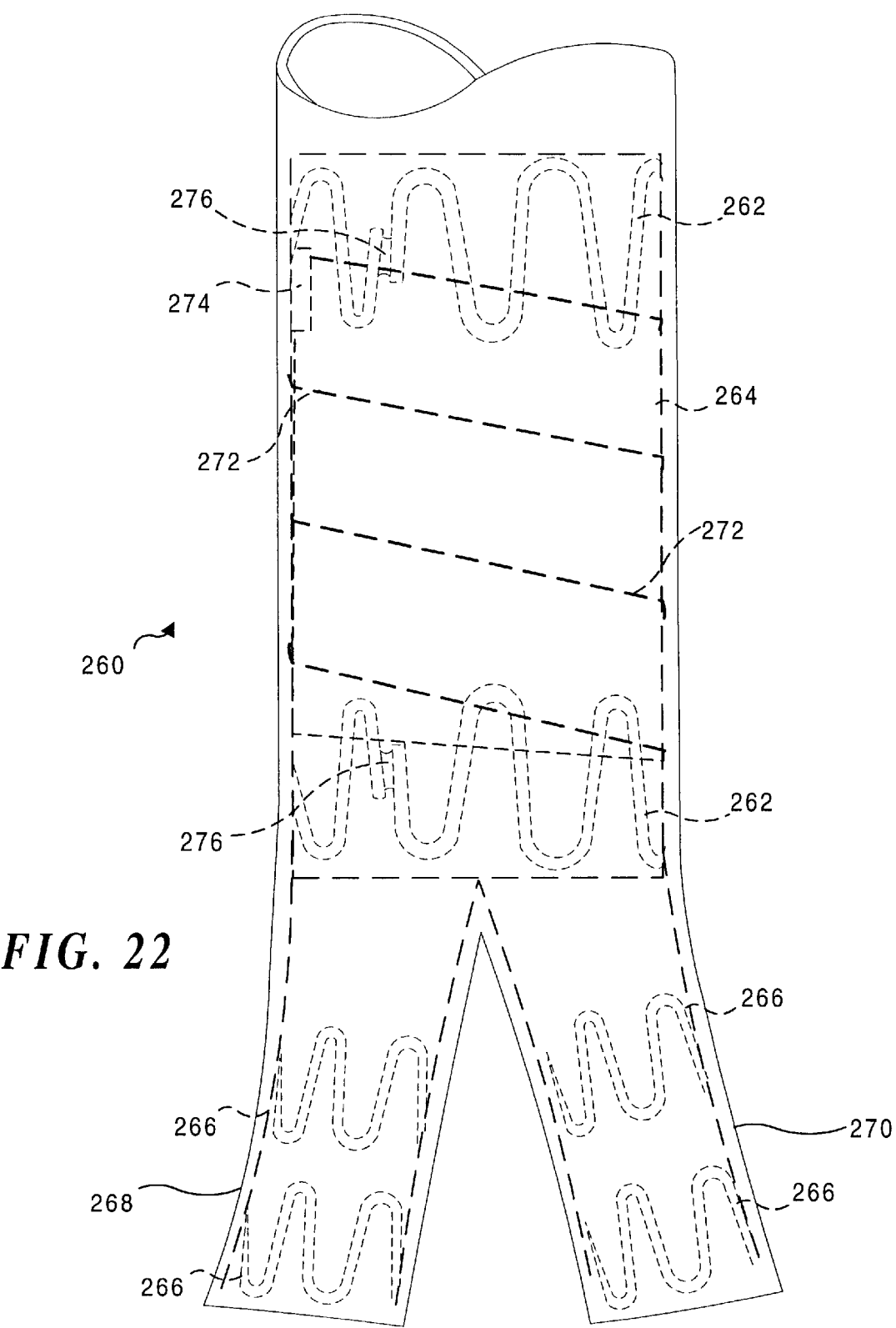
FIG. 22 is side elevational view of a portion of a branching artery in which a graft stent that is used for monitoring one or more parameters is implanted.

FIG. 22 illustrates a stent graft (or spring graft) 260 that includes the present invention. A stent graft differs from a conventional synthetic graft in the method of delivery. Conventional grafts are installed surgically, while stent grafts are installed using an endovascular delivery system. The entire stent graft assembly must be collapsible onto a delivery catheter (not shown). At a minimum, the stent graft comprises a synthetic graft section with an expandable stent disposed at one or both ends. The stent retains the graft in position. Some stent grafts have stents along the entire length of the graft section, and some may include metal hooks at one or both ends to firmly attach the graft to the vessel wall.

Stent graft 260 is of a type that is used to repair arteries near a bifurcation of the artery into two small branches 268 and 270. However, it should be noted that the present invention can be used with almost any type of stent graft and is not in any way limited to the bifurcated type shown in the figure. The TALENT spring graft system available from World Medical Manufacturing is similar to stent graft 260. The term "spring graft" is apparently used with this type of stent graft because the stent portion is self-expanding, comprising Nitinol springs 262 and 266 that are embedded into polyester (DACRON) or PTFE graft material 264. The larger diameter aortic section is DACRON, and the smaller branch portions are PTFE. The graft material is stitched to the Nitinol springs. A balloon (not shown) is included in the delivery system to perform one or more functions, including expansion of the spring assembly, placement at the desired location, flow occlusion, and straightening blood vessels to aid advancement of the assembly to the desired location. Electrically insulating ceramic weld joints 276 couple sections of each spring to break any current loop that would reduce the efficiency of the RF coupling. An insulated wire 272 is wound around the outside of a graft 264 and is preferably formed of kinked or zigzag wire to enable graft expansion. Wire 272 is coupled to a sensor/electronic circuit 274. A stent graft suitable for use in the embodiment shown in FIG. 22 is made by Sulzer Vascutek and W. L. Gore. The ANEURX stent graft from Medtronic, and the WALLGRAFT stent graft from Medivent-Schneider, which includes a woven mesh stent within its wall, are also suitable for this embodiment.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. An endoluminal implant adapted to be inserted into a body passage and to determine a condition of fluid flow through the endoluminal implant within the body passage, comprising:
   (a) a generally tubular shaped member having two states, including a compact state in which the member has a first cross-sectional size and an expanded state in which the member has a second cross-sectional size, said second cross-sectional size being substantially greater than said first cross-sectional size, said member including an electrical conductor;
   (b) a sensor that is adapted to monitor a parameter related to fluid flow through said member, producing a signal indicative of said parameter; and
   (c) a data transmitter coupled to the sensor to receive the signal, said data transmitter also being coupled to the member and adapted to transmit electromagnetic data corresponding to the signal outside the body passage in which the endoluminal implant is installed, using the electrical conductor of the member as an antenna.

2. The endoluminal implant of claim 1, further comprising an external coil adapted to be disposed proximate to the member, but outside the body passage, said external coil receiving the electromagnetic data transmitted from the member.

3. The endoluminal implant of claim 2, further comprising a monitor that is coupled to the external coil for displaying an indication of the parameter, as a function of the electromagnetic data, said monitor including a power source, said external coil electromagnetically transferring electrical power to the electrical antenna from the power source.

4. The endoluminal implant of claim 1, wherein the member comprises a spiral winding.

5. The endoluminal implant of claim 1, wherein the member comprises a helical braid.

6. The endoluminal implant of claim 1, wherein the sensor comprises an ultrasonic transmitter that produces an ultrasonic waveform directed through an interior portion of the member, said ultrasonic waveform being affected by a fluid flowing through the interior portion of the member to provide an indication of the condition of the fluid flow through the member.

7. The endoluminal implant of claim 6, wherein the ultrasonic transmitter also operates as an ultrasonic receiver, to receive an echo of the ultrasonic waveform that is reflected from the fluid flow through the member.

8. The endoluminal implant of claim 6, wherein the sensor further comprises an ultrasonic receiver that receives the ultrasonic waveform produced by the transmitter after said ultrasonic waveform is affected by the fluid flow through the member, said ultrasonic receiver producing the signal indicative of the parameter.

9. The endoluminal implant of claim 8, wherein the ultrasonic transmitter and ultrasonic receiver each comprise a conformal array of a plurality of spaced-apart, flexible transducer elements that have a curved configuration generally conforming to a curvature of the member, said conformal arrays being disposed either inside or outside of the member, and said conformal array for the ultrasonic transmitter being configured so that it produces ultrasonic waveforms, which propagate through the interior portion of the member in a predefined direction relative to a longitudinal axis of the member.

10. The endoluminal implant of claim 6, wherein the parameter is one of a fluid velocity and a fluid volumetric flow rate.

11. The endoluminal implant of claim 8, wherein the ultrasonic receiver is disposed on an opposite side of the member from where the ultrasonic transmitter is disposed.

12. The endoluminal implant of claim 1, wherein the sensor comprises a distal and a proximal pressure transducer, said distal pressure transducer being exposed to a fluid pressure of the fluid flow through an interior portion of the member adjacent to where the fluid exits the member and said proximal pressure transducer being exposed to a fluid pressure of the fluid flow through the interior portion of the member adjacent to where the fluid enters the member, said signal being indicative of a differential pressure corresponding to a difference between a proximal and a distal pressure respectively sensed by the proximal and distal pressure transducers.

13. The endoluminal implant of claim 1, wherein the endoluminal implant comprises a stent.

14. The endoluminal implant of claim 1, wherein the endoluminal implant comprises a stent graft.

15. The endoluminal implant of claim 1, wherein the electrical conductor is generally coiled about the member in a plurality of turns, to form the antenna.

16. The endoluminal implant of claim 15, wherein the member includes a break point at a joint fastened with a nonconductive material, said break point preventing the member from acting as a shorted turn that would reduce an efficacy of the antenna.

17. An endoluminal implant adapted to inserted into a body passage to monitor a parameter within the body passage, comprising:

(a) a generally tubular shaped member that is expandable within a body passage, said member including an electrical conductor that comprises an antenna;

(b) a sensor disposed on the member and adapted to sense the parameter, producing a signal indicative of said parameter; and (c) a data transmitter affixed to the member and coupled to the sensor to receive the signal, said data transmitter being also adapted to transmit electromagnetic data corresponding to the signal through the antenna and outside the body passage in which the endoluminal implant is adapted to be installed.

18. The endoluminal implant of claim 17, wherein the antenna is adapted to electromagnetically couple to a source of electrical power that is outside the body passage, said electrical power providing an electrical current used to energize at least one of the data transmitter and the sensor.

19. The endoluminal implant of claim 17, wherein the parameter monitored by the sensor is indicative of a condition of fluid flow through an interior portion of the member, including one of flow velocity and volumetric rate of flow.

20. The endoluminal implant of claim 19, wherein the sensor comprises an ultrasonic transducer that produces an ultrasonic waveform, which is affected by a fluid flow within the endoluminal implant and the body passage.

21. The endoluminal implant of claim 17, wherein the sensor is adapted to be exposed to a fluid flowing through an interior portion of the member, the parameter monitored by the sensor comprising a physiological metabolite level in the fluid flowing through the interior portion of the member.

22. The endoluminal implant of claim 17, wherein the sensor comprises a pressure transducer that determines a pressure of the fluid flowing through an interior portion of the member.

23. The endoluminal implant of claim 17, wherein the sensor comprises a strain sensor that monitors displacement of disparate points that are spaced apart about the member.

24. The endoluminal implant of claim 17, wherein the sensor is adapted to monitor a property of organic matter disposed adjacent to or within the member to determine a type of the organic matter.

25. The endoluminal implant of claim 17, wherein the member further comprises a heater and wherein the sensor comprises a plurality of temperature sensors that determine a differential temperature between at least two of the temperature sensors.

26. The endoluminal implant of claim 25, wherein the heater heats the fluid at a modulated periodically varying rate, further comprising a filter for filtering the differential temperature, producing a filtered signal from which the signal is derived, said signal being indicative of a velocity of a fluid flow through the member.

27. The endoluminal implant of claim 17, wherein the member includes a helical element that expands outwardly to increase a size of the body passage, said electrical conductor comprising at least a portion of the helical element.

28. The endoluminal implant of claim 17, further comprising a plurality of sensors disposed on the member at a corresponding plurality of spaced-apart locations and adapted to sense the parameter at the corresponding plurality of locations or to monitor a plurality of different parameters, each of the plurality of sensors producing a signal indicative of the parameter that it senses.

29. The endoluminal implant of claim 28, wherein the member further comprises a plurality of separate electrical conductors and a plurality of data transmitters each separately connected to a different one of the electrical conductors, and wherein the plurality of sensors are each coupled to a different one of the plurality of data transmitters, each of said plurality of data transmitters transmitting the signal produced by the sensor coupled to that data transmitter through the electrical conductor connected to that data transmitter.

30. The endoluminal implant of claim 26, wherein the member further comprises a plurality of electrical conductors connected in series and a plurality of data transmitters connected to at least one of the electrical conductors, and wherein the plurality of sensors are each coupled to a different one of the plurality of data transmitters, each of said plurality of data transmitters transmitting the signal produced by the sensor coupled to that data transmitter through the electrical conductors.

31. The endoluminal implant of claim 17, wherein the electrical conductor is configured in a saddle-shaped coil around a portion of the member.

32. The endoluminal implant of claim 17, wherein the electrical conductor crosses over itself in a plurality of locations about the member and is insulated to avoid electrical conduction where it crosses over itself at least at some of said locations.

33. The endoluminal implant of claim 17, wherein the endoluminal implant comprises a stent.

34. The endoluminal implant of claim 17, wherein the endoluminal implant comprises a stent graft.

35. The endoluminal implant of claim 17, wherein the conductor is coiled about the member.

36. The endoluminal implant of claim 35, wherein the member includes a break point at a joint fastened with a nonconductive material, said break point preventing the member from acting as a shorted turn that would reduce an efficacy of the antenna.

37. A method for conveying a parameter sensed in a vicinity of an endoluminal implant, which is adapted to be moved to a treatment site inside a body passage, to an external location disposed outside the body passage, comprising the steps of:

(a) sensing the parameter within the body passage, producing a signal indicative of the parameter;

(b) connecting the signal to an electrical conductor comprising the endoluminal implant;

(c) electromagnetically coupling the signal from the electrical conductor to the external location; and (d) receiving the signal at the external location to monitor the signal.

38. The method of claim 37, wherein the step of sensing the parameter comprises the steps of:

(a) producing an ultrasonic waveform that is directed into the body passage, said ultrasonic waveform being affected by a fluid flow through the body passage;

(b) receiving the ultrasonic waveform after it is affected by the fluid flow in the body passage; and (c) producing the signal as a function of the ultrasonic waveform affected by the fluid flow, so that the parameter indicated by the signal is one of a fluid flow velocity and a fluid flow rate.

39. The method of claim 37, wherein the electrical conductor comprises at least a portion of a spiral element of the endoluminal implant that is adapted to apply a radially outward-directed force against deposits disposed on an interior surface of the body passage.

40. The method of claim 37, wherein the electrical conductor comprises at least a portion of a mesh that is adapted to apply a radially outward-directed force against deposits disposed on an interior surface of the body passage.

41. The method of claim 37, further comprising the step of electromagnetically coupling electrical power from the external location into the electrical conductor, said electrical power being used to provide power for electromagnetically coupling the signal from the electrical conductor to the external location.

42. The method of claim 37, wherein the step of sensing the parameter comprises the step of exposing a biochemical sensor responsive to organic substances to a biological fluid flowing through the body passage.

43. The method of claim 37, wherein the step of sensing the parameter comprises the step of providing a strain sensor to monitor stress between spaced-apart points on the endoluminal implant.

44. The method of claim 37, wherein the step of sensing the parameter comprises the step of providing a pressure transducer to monitor pressure of a fluid flowing inside the endoluminal implant.

45. The method of claim 37, wherein the step of sensing the parameter comprises the step of providing a temperature sensor to monitor a temperature in the vicinity of the endoluminal implant.

46. The method of claim 37, wherein the step of sensing the parameter comprises the step of providing a deposit and ingrowth sensor for detecting fatty deposits and tissue ingrowth within an interior portion of the endoluminal implant.

47. The method of claim 46, wherein the deposit and ingrowth sensor senses a permittivity of any tissue disposed within the interior portion of the endoluminal implant.

48. The method of claim 46, wherein the deposit and ingrowth sensor senses at least one of a resistance and a capacitance of any tissue disposed within the interior of the endoluminal implant.

49. The method of claim 37, wherein the parameter that is sensed determines a state of fluid flow through the endoluminal implant.

50. The method of claim 49, further comprising the step of providing a conformal array of ultrasonic transducer elements that extends at least partly around the endoluminal implant and is carried on a band that elastically distorts with the endoluminal implant when it is being inserted into the body passage.

51. The method of claim 37, wherein the external location is disposed proximate to and outside of a wall of the body passage.

52. The method of claim 37, wherein the external location is disposed outside a body of a patient in which the endoluminal implant is implanted.

53. The method of claim 37, wherein the endoluminal implant comprises a stent.

54. The method of claim 37, wherein the endoluminal implant comprises a stent graft.

* * * * *